(12) United States Patent
Ferrie et al.

(10) Patent No.: US 11,584,906 B2
(45) Date of Patent: Feb. 21, 2023

(54) CELL CULTURE VESSEL FOR 3D CULTURE AND METHODS OF CULTURING 3D CELLS

(71) Applicant: CORNING INCORPORATED, Corning, NY (US)

(72) Inventors: Ann MeeJin Ferrie, Painted Post, NY (US); Vasiliy Nikolaevich Goral, Painted Post, NY (US); Jeffrey Glenn Lynn, Wellsboro, PA (US)

(73) Assignee: CORNING INCORPORATED, Corning, NY (US)

( * ) Notice: Subject to any disclaimer, the term of this patent is extended or adjusted under 35 U.S.C. 154(b) by 185 days.

(21) Appl. No.: 16/628,309

(22) PCT Filed: Jul. 13, 2018

(86) PCT No.: PCT/US2018/042115
§ 371 (c)(1),
(2) Date: Jan. 3, 2020

(87) PCT Pub. No.: WO2019/014610
PCT Pub. Date: Jan. 17, 2019

(65) Prior Publication Data
US 2020/0148989 A1 May 14, 2020

Related U.S. Application Data

(60) Provisional application No. 62/642,400, filed on Mar. 13, 2018, provisional application No. 62/532,639, (Continued)

(51) Int. Cl.
*C12M 1/24* (2006.01)
*C12M 1/32* (2006.01)
(Continued)

(52) U.S. Cl.
CPC ........... *C12M 23/08* (2013.01); *B01L 3/5085* (2013.01); *C12M 23/12* (2013.01); *B01L 2300/0858* (2013.01); *C12N 5/0062* (2013.01)

(58) Field of Classification Search
CPC ..... C12M 23/08; C12M 23/12; C12N 5/0062; B01L 3/5085; B01L 2300/0858
See application file for complete search history.

(56) References Cited

U.S. PATENT DOCUMENTS 2,947,116 A 8/1960 Earle et al.
3,630,849 A 12/1971 Land et al.
(Continued)

FOREIGN PATENT DOCUMENTS

AU 2004256209 A1 1/2005
CA 2558946 A1 1/2005
(Continued)

OTHER PUBLICATIONS

International Search Report and Written Opinion of the International Searching Authority; PCT/US2018/042115; dated Oct. 16, 2018; 12 Pages; European Patent Office.
(Continued)

*Primary Examiner* — Michael L Hobbs
(74) *Attorney, Agent, or Firm* — Michael G. Panian

(57) ABSTRACT

A cell culture vessel (100) has walls and a substrate having a plurality of microcavities (120), where each microcavity of the plurality of microcavities includes a concave well and an opening to allow the microcavity to be filled with liquid. A flange (170) surrounds the substrate having an array of microcavities. A channel (175, 176) surrounds the flange, providing a moat around the microcavity substrate. The flange is angled. Methods of culturing cells in the cell culture vessel are also provided.

9 Claims, 17 Drawing Sheets

Related U.S. Application Data filed on Jul. 14, 2017, provisional application No. 62/532,671, filed on Jul. 14, 2017, provisional application No. 62/532,648, filed on Jul. 14, 2017.

(51) Int. Cl.
  *B01L 3/00* (2006.01)
  *C12N 5/00* (2006.01)

(56) References Cited

U.S. PATENT DOCUMENTS

| | | |
|---|---|---|
| 4,382,685 A | 5/1983 | Pearson |
| 4,670,396 A | 6/1987 | Bear et al. |
| 4,927,764 A | 5/1990 | Lyman et al. |
| 4,980,293 A | 12/1990 | Jeffs |
| 5,047,347 A | 9/1991 | Cline |
| 5,151,366 A | 9/1992 | Serkes et al. |
| 5,171,994 A | 12/1992 | Bahraman |
| 5,171,995 A | 12/1992 | Gast et al. |
| 5,240,854 A | 8/1993 | Berry et al. |
| 5,272,084 A | 12/1993 | O'Connell et al. |
| 5,374,557 A | 12/1994 | Verma |
| 5,398,837 A | 3/1995 | Degrassi |
| 5,487,872 A | 1/1996 | Hafeman et al. |
| 5,554,536 A | 9/1996 | Rising |
| 5,598,262 A | 1/1997 | Jutard et al. |
| 5,665,562 A | 9/1997 | Cook |
| 5,693,537 A | 12/1997 | Wilson et al. |
| 5,707,869 A | 1/1998 | Wolf et al. |
| 5,710,043 A | 1/1998 | Pay |
| 5,736,397 A | 4/1998 | Garcia et al. |
| 5,759,494 A | 6/1998 | Szlosek |
| 5,772,905 A | 6/1998 | Chou |
| 5,783,440 A | 7/1998 | Stevens |
| 5,792,653 A | 8/1998 | Weibezahn et al. |
| 5,858,309 A | 1/1999 | Mathus et al. |
| 5,972,694 A | 10/1999 | Mathus |
| 6,030,829 A | 2/2000 | Dannoux et al. |
| 6,039,972 A | 3/2000 | Barlow et al. |
| 6,306,646 B1 | 10/2001 | Saad et al. |
| 6,348,999 B1 | 2/2002 | Summersgill et al. |
| 6,514,464 B1 | 2/2003 | Knebel |
| 6,521,451 B2 | 2/2003 | Potter |
| 6,567,675 B1 | 5/2003 | Rosen et al. |
| 6,767,607 B2 | 7/2004 | Tanner et al. |
| 6,811,752 B2 | 11/2004 | Barbera-Guillem |
| 6,908,767 B2 | 6/2005 | Bader |
| 7,470,424 B2 | 12/2008 | Kataoka et al. |
| 7,547,547 B2 | 6/2009 | Dang et al. |
| 7,674,346 B2 | 3/2010 | Clements et al. |
| 7,687,262 B2 | 3/2010 | Cattadoris |
| 7,691,369 B2 | 4/2010 | Kataoka et al. |
| 7,727,759 B2 | 6/2010 | Ozawa et al. |
| 7,745,209 B2 | 6/2010 | Martin et al. |
| 7,745,210 B2 | 6/2010 | Martin |
| 7,897,379 B2 | 3/2011 | Kenney et al. |
| 7,919,319 B2 | 4/2011 | Jervis et al. |
| 8,053,230 B2 | 11/2011 | Whittlinger |
| 8,143,053 B2 | 3/2012 | Yerbic |
| 8,148,152 B2 | 4/2012 | Kolossov et al. |
| 8,158,426 B2 | 4/2012 | Wilson et al. |
| 8,158,427 B2 | 4/2012 | Wilson et al. |
| 8,163,537 B2 | 4/2012 | Martin et al. |
| 8,168,432 B2 | 5/2012 | Wilson et al. |
| 8,178,345 B2 | 5/2012 | Bennett et al. |
| 8,273,572 B2 | 9/2012 | Martin et al. |
| 8,318,479 B2 | 11/2012 | Domansky et al. |
| 8,415,144 B2 | 4/2013 | Wilson et al. |
| 8,470,589 B2 | 6/2013 | Martin et al. |
| D685,497 S | 7/2013 | Kenney et al. |
| 8,486,692 B2 | 7/2013 | Simon |
| 8,597,597 B2 | 12/2013 | Deutsch et al. |
| 8,617,879 B2 | 12/2013 | Yu et al. |
| 8,697,443 B2 | 4/2014 | Wilson et al. |
| 8,759,017 B2 | 6/2014 | Owen et al. |
| 8,778,669 B2 | 7/2014 | Lacey et al. |
| 8,846,399 B2 | 9/2014 | Martin et al. |
| 8,906,685 B2 | 12/2014 | Takayama et al. |
| 8,932,544 B2 | 1/2015 | Mueller et al. |
| 9,039,883 B2 | 5/2015 | Guerrieri et al. |
| 9,040,293 B2 | 5/2015 | Gulzow et al. |
| 9,045,721 B2 | 6/2015 | Martin et al. |
| 9,068,281 B2 | 6/2015 | Wu et al. |
| 9,126,199 B2 | 9/2015 | Moritz et al. |
| 9,169,460 B2 | 10/2015 | Cecchi |
| D748,812 S | 2/2016 | Kenney et al. |
| 9,260,684 B1 | 2/2016 | Egeler et al. |
| 9,260,695 B2 | 2/2016 | Crowley et al. |
| 9,493,733 B2 | 11/2016 | Giles |
| 9,494,577 B2 | 11/2016 | McGarr et al. |
| 9,573,128 B1 | 2/2017 | McClelland |
| 9,587,213 B2 | 3/2017 | Morgan et al. |
| 9,732,317 B2 * | 8/2017 | Wilson ................ C12M 23/24 |
| 9,790,465 B2 | 10/2017 | Bennett et al. |
| 9,845,451 B2 | 12/2017 | Martin et al. |
| 9,862,918 B2 | 1/2018 | Ito |
| 10,254,274 B2 | 4/2019 | Miklas et al. |
| 2002/0022219 A1 | 2/2002 | Clements et al. |
| 2002/0172621 A1 | 11/2002 | Barbera-Guillem |
| 2003/0031829 A1 | 2/2003 | Tanner et al. |
| 2003/0104494 A1 | 6/2003 | Ravkin et al. |
| 2003/0183958 A1 | 10/2003 | Goff et al. |
| 2003/0186217 A1 | 10/2003 | Bader |
| 2003/0215941 A1 | 11/2003 | Campbell et al. |
| 2004/0091397 A1 | 5/2004 | Picard |
| 2004/0101955 A1 | 5/2004 | Whitley |
| 2004/0125266 A1 | 7/2004 | Miyauchi et al. |
| 2004/0216835 A1 | 11/2004 | Tanner et al. |
| 2004/0259242 A1 | 12/2004 | Malinge et al. |
| 2004/0259423 A1 * | 12/2004 | Elbaz ................ G06K 19/07733 439/660 |
| 2005/0032208 A1 | 2/2005 | Oh et al. |
| 2005/0047971 A1 | 3/2005 | Clements et al. |
| 2005/0112030 A1 | 5/2005 | Gaus |
| 2005/0116717 A1 | 6/2005 | Dransfield et al. |
| 2005/0147959 A1 | 7/2005 | Frondoza et al. |
| 2006/0110822 A1 | 5/2006 | Robbins et al. |
| 2006/0234370 A1 | 10/2006 | Korpinen et al. |
| 2006/0252044 A1 | 11/2006 | Okumura et al. |
| 2006/0292654 A1 | 12/2006 | Reardon |
| 2007/0178441 A1 | 8/2007 | Li |
| 2007/0216897 A1 | 9/2007 | Sonda |
| 2008/0003671 A1 | 1/2008 | Martin |
| 2008/0009027 A1 | 1/2008 | Fraker et al. |
| 2008/0118974 A1 | 5/2008 | Martin et al. |
| 2008/0206857 A1 | 8/2008 | Kenney et al. |
| 2008/0297784 A1 | 12/2008 | Leblanc et al. |
| 2008/0299649 A1 | 12/2008 | Martin et al. |
| 2008/0300278 A1 | 12/2008 | Torrens et al. |
| 2009/0017540 A1 | 1/2009 | Nishio et al. |
| 2009/0018033 A1 | 1/2009 | Morgan et al. |
| 2009/0029462 A1 | 1/2009 | Beardsley et al. |
| 2009/0037293 A1 | 2/2009 | Unger et al. |
| 2009/0170190 A1 | 7/2009 | Nishi et al. |
| 2009/0191620 A1 | 7/2009 | Martin et al. |
| 2009/0288963 A1 | 11/2009 | Guerrieri et al. |
| 2009/0298164 A1 * | 12/2009 | Cattadoris ............ C12M 23/24 435/294.1 |
| 2009/0298166 A1 | 12/2009 | Fang et al. |
| 2010/0055774 A1 | 3/2010 | Wilson |
| 2010/0068793 A1 | 3/2010 | Ungrin et al. |
| 2010/0093075 A1 | 4/2010 | Muller |
| 2010/0112014 A1 | 5/2010 | Gilbert et al. |
| 2010/0112684 A1 | 5/2010 | Lee et al. |
| 2010/0119418 A1 | 5/2010 | Clements et al. |
| 2010/0170790 A1 | 7/2010 | Takahashi et al. |
| 2010/0190197 A1 | 7/2010 | Martin et al. |
| 2010/0197013 A1 | 8/2010 | Kamp et al. |
| 2010/0247386 A1 | 9/2010 | Deutsch et al. |
| 2010/0273258 A1 | 10/2010 | Lannutti et al. |
| 2010/0297600 A1 | 11/2010 | Cecchi |
| 2011/0086375 A1 | 4/2011 | Ungrin et al. |
| 2011/0097790 A1 | 4/2011 | Yerbic |
| 2011/0129923 A1 | 6/2011 | Wilson et al. |

(56) References Cited

U.S. PATENT DOCUMENTS

| | | |
|---|---|---|
| 2011/0229961 A1 | 9/2011 | Higashi et al. |
| 2012/0064627 A1 | 3/2012 | Khine et al. |
| 2012/0129208 A1 | 5/2012 | Khine et al. |
| 2012/0129257 A1 | 5/2012 | Yu et al. |
| 2012/0219572 A1 | 8/2012 | Prockop et al. |
| 2013/0122539 A1 | 5/2013 | Li et al. |
| 2013/0122580 A1 | 5/2013 | Tsukada et al. |
| 2013/0143254 A1 | 6/2013 | Thomas et al. |
| 2013/0164848 A1 | 6/2013 | Munaka et al. |
| 2013/0203159 A1 | 8/2013 | Itoh et al. |
| 2013/0344598 A1 | 12/2013 | Nistor |
| 2014/0004086 A1 | 1/2014 | Peak |
| 2014/0027784 A1 | 1/2014 | Wada et al. |
| 2014/0099717 A1 | 4/2014 | Fraker et al. |
| 2014/0106394 A1 | 4/2014 | Ko et al. |
| 2014/0106452 A1 | 4/2014 | Vukasinovic |
| 2014/0120573 A1 | 5/2014 | Tavana et al. |
| 2014/0178992 A1 | 6/2014 | Nakashima et al. |
| 2014/0221225 A1 | 8/2014 | Danen et al. |
| 2014/0226004 A1 | 8/2014 | Son et al. |
| 2014/0227784 A1 | 8/2014 | Ejiri et al. |
| 2014/0315296 A1 | 10/2014 | Wilson |
| 2014/0322806 A1 | 10/2014 | Bennett et al. |
| 2015/0004686 A1 | 1/2015 | Goral et al. |
| 2015/0064738 A1 | 3/2015 | Tsukada et al. |
| 2015/0072405 A1 | 3/2015 | Ito |
| 2015/0184119 A1 | 7/2015 | Tsukada et al. |
| 2015/0247112 A1 | 9/2015 | Orr et al. |
| 2016/0003796 A1 | 1/2016 | Kranbuehl |
| 2016/0017267 A1 | 1/2016 | Hansen et al. |
| 2016/0040120 A1 | 2/2016 | Gottwald et al. |
| 2016/0137962 A1 | 5/2016 | Ejiri et al. |
| 2016/0194588 A1 | 7/2016 | Guenat et al. |
| 2016/0216250 A1 | 7/2016 | Ritter et al. |
| 2017/0067019 A1* | 3/2017 | Ho ............................ C12M 3/00 |
| 2017/0073625 A1 | 3/2017 | Kasuto et al. |
| 2017/0226455 A1 | 8/2017 | Fang et al. |
| 2017/0283757 A1 | 10/2017 | Carter et al. |
| 2017/0306281 A1 | 10/2017 | Martin et al. |
| 2017/0342363 A1* | 11/2017 | Fang ....................... C12M 3/065 |
| 2018/0166743 A1 | 6/2018 | Lee et al. |
| 2018/0201888 A1 | 7/2018 | Miwa et al. |
| 2018/0301754 A1 | 10/2018 | Badding et al. |
| 2019/0006707 A1 | 1/2019 | Sakamoto et al. |
| 2020/0239854 A1 | 7/2020 | Ayano et al. |

FOREIGN PATENT DOCUMENTS

| | | |
|---|---|---|
| CA | 2679011 A1 | 9/2008 |
| CA | 2848875 A1 | 3/2013 |
| CN | 2186755 Y | 1/1995 |
| CN | 1234112 A | 11/1999 |
| CN | 1875093 A | 12/2006 |
| CN | 201626959 U | 11/2010 |
| CN | 101978041 A | 2/2011 |
| CN | 102105578 A | 6/2011 |
| CN | 102257123 A | 11/2011 |
| CN | 102449135 A | 5/2012 |
| CN | 202450098 U | 9/2012 |
| CN | 202849407 U | 4/2013 |
| CN | 103080294 A | 5/2013 |
| CN | 103119151 A | 5/2013 |
| CN | 203513696 U | 4/2014 |
| CN | 103814125 A | 5/2014 |
| CN | 204608026 U | 9/2015 |
| CN | 204702760 U | 10/2015 |
| CN | 204714819 U | 10/2015 |
| CN | 204752742 U | 11/2015 |
| CN | 204803327 U | 11/2015 |
| CN | 205170866 U | 4/2016 |
| CN | 205669029 U | 11/2016 |
| CN | 205839030 U | 12/2016 |
| CN | 205990396 U | 3/2017 |
| DE | 8309876 U1 | 12/1983 |
| DE | 10019862 A1 | 11/2001 |
| DE | 202006017853 U1 | 2/2007 |
| DE | 102009005526 A1 | 7/2010 |
| DE | 102014214077 A1 | 1/2016 |
| DE | 102014017728 A1 | 6/2016 |
| EP | 307048 A2 | 3/1989 |
| EP | 0605527 A1 | 7/1994 |
| EP | 0681846 A2 | 11/1995 |
| EP | 0800571 A2 | 10/1997 |
| EP | 834552 A1 | 4/1998 |
| EP | 965633 A1 | 12/1999 |
| EP | 1181349 A1 | 2/2002 |
| EP | 1348533 A2 | 10/2003 |
| EP | 1445022 A2 | 8/2004 |
| EP | 1988152 A1 | 11/2008 |
| EP | 2032262 A2 | 3/2009 |
| EP | 2617807 A1 | 7/2013 |
| EP | 2653531 A1 | 10/2013 |
| EP | 2759592 A1 | 7/2014 |
| EP | 2896684 A1 | 7/2015 |
| EP | 3081627 A1 | 10/2016 |
| EP | 3296018 A1 | 3/2018 |
| EP | 3351615 A1 | 7/2018 |
| EP | 3372666 A1 | 9/2018 |
| GB | 2147100 A | 5/1985 |
| JP | 03-139350 A | 6/1991 |
| JP | 06-038734 A | 2/1994 |
| JP | 06327462 A | 11/1994 |
| JP | 09173049 A | 7/1997 |
| JP | 09-234811 A | 9/1997 |
| JP | 10210866 A | 8/1998 |
| JP | 10210966 A | 8/1998 |
| JP | 2001-106749 A | 4/2001 |
| JP | 2003135056 A | 5/2003 |
| JP | 2003180335 A | 7/2003 |
| JP | 2004129558 A | 4/2004 |
| JP | 2006-121991 A | 5/2006 |
| JP | 2006-191809 A | 7/2006 |
| JP | 2007-510429 A | 4/2007 |
| JP | 3139350 U | 2/2008 |
| JP | 2009-017810 A | 1/2009 |
| JP | 2009050194 A | 3/2009 |
| JP | 2009-183288 A | 8/2009 |
| JP | 2009-542230 A | 12/2009 |
| JP | 2010088347 A | 4/2010 |
| JP | 2010104327 A | 5/2010 |
| JP | 2010-518879 A | 6/2010 |
| JP | 2010158214 A | 7/2010 |
| JP | 2011-509686 A | 3/2011 |
| JP | 2011-521642 A | 7/2011 |
| JP | 2011172533 A | 9/2011 |
| JP | 2011-528226 A | 11/2011 |
| JP | 2012249547 A | 12/2012 |
| JP | 2013055911 A | 3/2013 |
| JP | 2014132869 A | 7/2014 |
| JP | 2015012827 A | 1/2015 |
| JP | 2015-029431 A | 2/2015 |
| JP | 2015073520 A | 4/2015 |
| JP | 5845185 B2 | 1/2016 |
| JP | 2016-136920 A | 8/2016 |
| JP | 2016136921 A | 8/2016 |
| JP | 2017-532970 A | 11/2017 |
| JP | 2018-108032 A | 7/2018 |
| KR | 1020140113139 A | 9/2014 |
| KR | 10-2014-0125662 A | 10/2014 |
| KR | 10-2017-0008539 A | 1/2017 |
| WO | 1992007063 A2 | 4/1992 |
| WO | 93/07258 A1 | 4/1993 |
| WO | 96/21851 A2 | 7/1996 |
| WO | 9815355 A2 | 4/1998 |
| WO | 1998031466 A1 | 7/1998 |
| WO | 2001080997 A1 | 11/2001 |
| WO | 2001092462 A1 | 12/2001 |
| WO | 2004/044120 A2 | 5/2004 |
| WO | 2004/094060 A1 | 11/2004 |
| WO | 2005047464 A2 | 5/2005 |
| WO | 2006043267 A1 | 4/2006 |
| WO | 2007/015770 A1 | 2/2007 |
| WO | 2007097120 A1 | 8/2007 |
| WO | 2008/006104 A2 | 1/2008 |

(56) References Cited

FOREIGN PATENT DOCUMENTS

| | | | |
|---|---|---|---|
| WO | 2008/008149 A2 | 1/2008 |
| WO | 2008/106771 A1 | 9/2008 |
| WO | 2008118500 A1 | 10/2008 |
| WO | 2008/140295 A1 | 11/2008 |
| WO | 2008/149039 A2 | 12/2008 |
| WO | 2008153783 A1 | 12/2008 |
| WO | 2009094125 A2 | 7/2009 |
| WO | 2009148509 A1 | 12/2009 |
| WO | 2009148512 A2 | 12/2009 |
| WO | 2010008566 A2 | 1/2010 |
| WO | 2010/042072 A1 | 4/2010 |
| WO | 2010/069589 A1 | 6/2010 |
| WO | 2012036011 A1 | 3/2012 |
| WO | 2012/077683 A1 | 6/2012 |
| WO | 2012170232 A1 | 12/2012 |
| WO | 2013042360 A1 | 3/2013 |
| WO | 2013/108293 A1 | 7/2013 |
| WO | 2013/116449 A1 | 8/2013 |
| WO | 2014/042162 A1 | 3/2014 |
| WO | 2014072432 A1 | 5/2014 |
| WO | 2014/140181 A1 | 9/2014 |
| WO | 2014156455 A1 | 10/2014 |
| WO | 2014165273 A1 | 10/2014 |
| WO | 2014171782 A1 | 10/2014 |
| WO | 2014/179196 A1 | 11/2014 |
| WO | 2014196204 A1 | 12/2014 |
| WO | 2015033507 A1 | 3/2015 |
| WO | 2015/061907 A1 | 5/2015 |
| WO | 2016064757 A1 | 4/2016 |
| WO | 2016069885 A1 | 5/2016 |
| WO | 2016069892 A1 | 5/2016 |
| WO | 2016069895 A1 | 5/2016 |
| WO | 2016069917 A1 | 5/2016 |
| WO | 2016069930 A1 | 5/2016 |
| WO | 2017025584 A1 | 2/2017 |
| WO | 2017/047735 A1 | 3/2017 |
| WO | 2017/077163 A1 | 5/2017 |
| WO | 2017142410 A1 | 8/2017 |
| WO | 2018/068034 A1 | 4/2018 |
| WO | 2018200893 A1 | 11/2018 |
| WO | 2019014621 A1 | 1/2019 |
| WO | 2019014627 A1 | 1/2019 |
| WO | 2019014635 A1 | 1/2019 |
| WO | 2019014636 A1 | 1/2019 |
| WO | 2019178039 A1 | 9/2019 |

OTHER PUBLICATIONS

Lovett et al. "Vascularization Strategies for Tissue Engineering" Tissue Engineering Part B, 2009, vol. 15, No. 3, pp. 353-370.
Office Action dated Aug. 8, 2019 pertaining to U.S. Appl. No. 15/708,473, filed Sep. 19, 2017, 20 pgs.
Achilli et al., "Advances in the Formation, Use and Understanding of Multi-Cellular Spheroids", Expert Opin. Biol. Ther. (2012) 12(10):1347-1360.
Alepee et al., "State-Of-The-Art 3D Cultures (Organs-On-A-Chip) in Safety Testing and Pathophysiology"; Transatlantic Think Tank for Toxicology, T4 Workshop Report, Altex 31, Apr. 2014, pp. 441-477, Retrieved From: http://dx.doi.org/10.14573/altex1406111 (Jul. 14, 2014).
Aline, "We Engineer Microfluidic Products"; 7 Pages; (2020) https://alineinc.com/.
G-Plate: Accelerate your cell cultures to the next dimension, "An original cell culture model allowing for island-shaped 3D cell aggregates", 1 page, retrieved Sep. 8, 2015.
Anada et al, "An Oxygen-Permeable Spheroid Culture System for the Prevention of Central Hypoxia and Necrosis of Spheroids"; Biomaterials 33 (2012) 8430-8441.
Bartosh et al, "Aggregation of Human Mesenchymal Stromal Cells (MSCS) Into 3D Spheroids Enhances Their Antiinflammatory Properties"; PNAS, Aug. 3, 2010, 107(31):13724-13729.

Bioivt Elevating Science® ; 6 Pages; (2020); http://www.hepregen.com/.
Carver et al, "Multicellular Tumor Spheroids as a Model for Assessing Delivery of Oligonucleotides in Three Dimensions"; Molecular Therapy-Nucleic Acids (2014) 3, E153; 8 Pages.
Chen et al, "Microfluidic array for three-dimensional perfusion culture of human mammary epithelial cells"; Biomedical Microdevices, 2011, 13(4):753-758.
Cheng et al, "MICRORNA-34a Targets Forkhead Box J2 to Modulate Differentiation of Endothelial Progenitor Cells in Response to Shear Stress", J Mol Cell Cardiol. 74 (2014) 4-12.
Choi et al, "Feasibility of a simple double-layered coculture system incorporating metabolic processes of the intestine and liver tissue: application to the analysis of benzo[a]pyrene toxicity", Toxicology in Vitro 18 (2004) 393-402.
CN-BIO, "Transforming Drug Discovery and the Lives of Patients"; 5 Pages; (2020) http://cn-bio.com/.
Colazzo et al, "Shear Stress and VEGF Enhance Endothelial Differentiation of Human Adipose-Derived Stem Cells", Growth Factors, 2014, 32(5):139-149.
Corning® HTS Transwell® -96 Tissue Culture Systems, Permeable Supports for High Throughput Screening Applications; 2 Pages (2004).
Tissue Dynamics, "Disruptive Drug Development"; 3 Pages; (Downloaded Mar. 9, 2020); https://www.tissuedynamics.com/.
Dolznig et al, "Organotypic spheroid cultures to study tumor-stroma interaction during cancer development", Drug Discovery Today: Disease Models, 2011, 8(2-3):113-118.
Domansky et al, "Perfused Multiwell Plate for 3D Liver Tissue Engineering", Lab Chip, 2010, 10:51-58.
Emulate, 6 Pages; (2019) https://emulatebio.com/.
Tissuse, "Emulating Human Biology, Pioneering Human-On-A-Chip Developments"; 1 Page; (Downloaded Mar. 9, 2020) https://www.tissuse.com/en/.
Endo et al, "Gene transfection to spheroid culture system on micropatterned culture plate by polyplex nanomicelle: a novel platform of genetically-modified cell transplantation", Drug Deliv. and Transl. Res., 2012, 2:398-405.
Engelberg et al, "Essential operating principles for tumor spheroid growth", BMC Systems Biology 2008, 2:110, 19 pages.
Friedrich et al, "Experimental anti-tumor therapy in 3-D: spheroids— old hat or new challenge?" Int J Radiat Biol 2007, 83(11-12):849-871.
Friedrich et al, "Spheroid-based drug screen: considerations and practical approach", Nature protocols, 2009, 4(3):309-323.
Frith et al, "Dynamic three-dimensional culture methods enhance mesenchymal stem cell properties and increase therapeutic potential", Tissue engineering, 2010, 16(4):735-749.
Fukuda et al, "Efficacy of a polyurethane foam/spheroid artificial liver by using human hepatoblastoma cell line (Hep G2)", Cell Transplantation, 2003, 12:51-58.
GeoCHEM Incorporated, Product Line; https://www.geocheminc.com, 4 Pages; (2020).
Haycock, "3D cell culture: a review of current approaches and techniques", Methods Mol Biol, 2011; 695:1-15.
Hirschhaeuser et al, "Multicellular tumor spheroids: An underestimated tool is catching up again", Journal of Biotechnology 148 (2010) 3-15.
Howes et al, "3-Dimensional Culture Systems for Anti-Cancer Compound Profiling and High-Throughput Screening Reveal Increases in EGFR Inhibitor-Mediated Cytotoxicity Compared to Monolayer Culture Systems"; PLOS One; Sep. 2004, 9(9), 11 Pages.
Hribar et al, "Nonlinear 3D Projection Printing of Concave Hydrogel Microstructures for Long-Term Multicellular Spheroid and Embryoid Body Culture"; Lab Chip, 2015, 15, 2412-2418.
Hwang et al, "Microwell-Mediated Control of Embryoid Body Size Regulates Embryonic Stem Cell Fate via Differential Expression of WNT5A and WNT11"; PNAS, 2009, 106(40):16978-16983.
HµREL® Corporation, Bioanalytic Tools Company; 2 Pages; (2013); http://hurelcorp.com/.

(56) References Cited

OTHER PUBLICATIONS

Jeon et al, "Combined Effects of Flow-Induced Shear Stress and Micropatterned Surface Morphology on Neuronal Differentiation of Human Mesenchymal Stem Cells" J Biosci Bioeng, 2014, 117(2):242-247.
Jiang et al, "Shear Enhances Thrombopoiesis and Formation of Microparticles That Induce Megakaryocytic Differentiation of Stem Cells", Blood, Sep. 25, 2014; 124(13):2094-2103.
Kelm et al, "Method for generation of homogeneous multicellular tumor spheroids applicable to a wide variety of cell types", Biotechnology and Bioengineering 2003; 83(2):173-180.
Kim et al, "Shear Stress Induced by an Interstitial Level of Slow Flow Increases the Osteogenic Differentiation of Mesenchymal Stem Cells Through Taz Activation" PLoS ONE, Mar. 21, 2014; 9(3), e92427, 9 pages.
Koide et al, "Formation of multicellular spheroids composed of adult rat hepatocytes in dishes with positively charged surfaces and under other nonadherent environments", Exp Cell Res 1990; 186:227-235.
Kunz-Schughart et al, "The use of 3-D cultures for high-throughput screening: the multicellular spheroid model", J Biomol Screen 2004, 9(4):273-285.
Kutsuzawa et al, "Highly Robust Protein Production by Co-Culture of CHO Spheroids Layered on Feeder Cells in Serum-Free Medium"; Colloid Polym Sci (2014) 292; 839-848.
Labusca, "Scaffold free 3D culture of mesenchymal stem cells; implications for regenerative medicine", J Transplant Stem Cel Biol 2015 2(1): 8.
Landry et al, "Spheroidal aggregate culture of rat liver cells: histotypic reorganization, biomatrix deposition, and maintenance of functional activities" J Cell Biol 1985; 101:914-923.
Lau et al, "Evaluation of a Novel in Vitro CACO-2 Hepatocyte Hybrid System for Predicting In Vivo Oral Bioavailability" Drug Metabolism and Disposition, vol. 32, No. 9, pp. 937-942, 2004.
Liquid Surge Control, LLC; "The Latest in Drop-In Baffle Technology"; 2 Pages; (2019).
Liu et al, "Quasi-spherical microwells on superhydrophobic substrates for long term culture of multicellular spheroids and high throughput assays" Biomaterials 35 (2014) pp. 6060-6068.
Liu et al, "Advanced Micromachining of Concave Microwells for Long Term On-Chip Culture of Multicellular Tumor Spheroids", ACS Appl. Mater. Interfaces, 2014, 6, 8090-8097.
Lu et al, "Galactosylated PVDF membrane promotes hepatocyte attachment and functional maintenance" Biomaterials 24 (2003) 4893-4903.
Markovitz-Bishitz, "A polymer microstructure array for the formation, culturing, and high throughput drug screening of breast cancer spheroids" Biomaterials 31 (2010) 8436-8444.
Messner et al, Multi-cell type human liver microtissues for hepatotoxicity testing. Archives of Toxicology, Nov. 11, 2012, 5 pages.
Elveflow; "Microfluidics Innovation Center"; 6 Pages; (Downloaded Mar. 9, 2020); https://www.elveflow.com/.
Mironov et al, "Organ Printing: Tissue Spheroids as Buliding Blocks" Biomaterials, 2009; 30(12): 2164-2174.
Moon et al, "Optimizing Human Embryonic Stem Cells Differentiation Efficiency by Screening Size-Tunable Homogenous Embryoid Bodies"; Biomaterials; 35 (2014) 5987-5997.
Urich et al, "Multicellular Self-Assembled Spheroidal Model of the Blood Brain Barrier"; Scientific Reports, 3, 1500, 8 Pages.
Murphy et al, "3D Bioprinting of Tissues and Organs"; Nature Biotechnology, vol. 32, No. 8, Aug. 2014, pp. 773-785.
Nortis; "Bridging the Gap Between In Vitro and In Vivo Research"; 16 Pages; (2015); https://www.nortisbio.com/.
Mimetas the Organ-On-A-Chip Company; "Organ-On-A-Chip Models for Science and Pharma"; 4 Pages; (Downloaded Mar. 9, 2020); https://mimetas.com/.
Otsuka et al, "Two-dimensional multiarray formation of hepatocyte spheroids on a microfabricated PEG-brush surface." ChemBioChem 2004; 5:850-855.

Peshwa et al, "Mechanistics of formation and ultrastructural evaluation of hepatocyte spheroids." In Vitro Cell Dev Biol Anim 1996; 32:197-203.
Organovo, "Pioneering Bioprinted Tissues to Treat Disease"; 2 Pages; (Downloaded Mar. 9, 2020) http://organovo.com/.
Rezende et al, "Scalable Biofabrication of Tissue Spheroids for Organ Printing"; Sciverse Science Direct, Procedia CIRP 5, (2013) 276-281.
Sa et al, "Round-bottomed Honeycomb Microwells: Embryoid body shape correlates with stem cell fate" Journal of Developmental Biology and Tissue Engineering vol. 4(2), pp. 12-22, May 2012.
Sakai et al, "Large-scale preparation and function of porcine hepatocyte spheroids." Int J Artif Organs 1996; vol. 19, No. 5, pp. 294-301.
Sakai et al, "Detachably Assembled Microfluidic Device for Perfusion Culture and Post-Culture Analysis of Spheroid Array"; Biotechnol. J. 2014, 9, 971-979.
Sakai et al, "Technique for the Control of Spheroid Diameter Using Microfabricated Chips"; Sciencedirect, Acta Biomaterialia 3 (2007) 1033-1040.
Sart et al, "Three-dimensional aggregates of mesenchymal stem cells: cellular mechanisms, biological properties and applications" Tissue engineering, 2013, Part B, vol. 00, No. 00, 1-16.
Satoh et al, "A Pneumatic Pressure-Driven Multi-Throughput Microfluidic Circulation Culture System" Lab Chip, 2016, 16, 2339-2348.
Seldon et al, "Evaluation of Encapsulated Liver Cell Spheroids in a Fluidised-Bed Bioartificial Liver for Treatment of Ischaemic Acute Liver Failure in Pigs in a Translational Setting"; PLOS One, 2013, 8(12), e82312.
Takezawa et al, "Morphological and immuno-cytochemical characterization of a hetero-spheroid composed of fibroblasts and hepatocytes" J Cell Sci 1992; 101:495-501.
Tara; "Innovating Predictive Cardiac Physiology"; 4 Pages; (2019) http://tarabiosystems.com/.
The Lab Depot® Products for Discovery Lab Supplies; Shake Flasks, 3 and 4 Baffles Product Information; 5 Pages (2019).
Tobe et al, "Receptor-mediated formation of multilayer aggregates of primary cultured adult rat hepatocytes on lactose-substituted polystyrene" Biochem Biophys Res Commun 1992; 184(1):225-230.
Tong et al, "Long-term culture of adult rat hepatocyte spheroids." Exp Cell Res 1992; 200:326-332.
Truckenmuller et al, Thermoforming of Film-Based Biomedical Microdevices, Adv. Mater. 2011, 23, pp. 1311-1329.
Tung et al, "High-throughput 3D spheroid culture and drug testing using 384 hanging drop array" Analyst, 2011, 136(3), 473-478.
Uchida et al, "An Injectable Spheroid System With Genetic Modification for Cell Transplantation Therapy"; Biomaterials, 35 (2014) 2499-2506.
Vinci et al, Advances in establishment and analysis of three-dimensional tumor spheroid-based functional assays for target validation and drug evaluation, BMC Biology 2012, 10:29.
Weegman et al, "Nutrient Regulation by Continuous Feeding Removes Limitations on Cell Yield in the Large-Scale Expansion of Mammalian Cell Spheroids"; PLOS One, 2013, vol. 8, Issue 10, e76611, 10 Pages.
Wikipedia, "Antiroll Tanks"; 3 Pages; Page Last Edited May 23, 2019.
Wrighton et al, "Forces of Change: Mechanics Underlying Formation of Functional 3D Organ Buds" Cell Stem Cell, May 7, 2015; 16(5): 453-454.
Xu et al, "Characterisation of some cytotoxic endpoints using rat liver and HepG2 spheroids as in vitro models and their application in hepatotoxicity studies. I. Glucose metabolism and enzyme release as cytotoxic markers." Toxicol Appl Pharmacol 2003;189:100-111.
Yamada et al, "Efficient induction of hepatocyte spheroids in a suspension culture using a water-soluble synthetic polymer as an artificial matrix." J Biochem 1998; 123:1017-1023.
AxoSIM, Nerve-On-A-Chip Mini-Brain About Team; 6 Pages; (Downloaded Mar. 9, 2020); http://axosim.com/.
Corning Life Sciences Product Portfolio; 5 Pages Saved Mar. 6, 2020.

(56) References Cited

OTHER PUBLICATIONS

Madoux et al, "Building Phenotypic 3D Spheroid HTS Assays to Identify Synthetic Lethal Small Molecule Inhibitors of KRAS"; The Scripps Research Institute Molecular Screening Center and Department of Cancer Biology, Scripps Florida, Jupiter, Florida, Department of Pathology, Jupiter Medical Center, Jupiter, Florida.

Stemcell Technologies, Reproducible and Uniform Embryoid Bodies Using AggreWell Plates, StemCell Technologies, Technical Manual Version 3.0.0, Mar. 2011, Catalog #29146, pp. 1-28.

"Laboratory Flasks Selection Guide: Types, Features, Applications", Engineering360, <https://www.globalspec.com/learnmore/labware_scientific_instruments/labware_consumables/laboratory_flasks#:~:text=Laboratory%20flasks%20are%20lab%20vessels,the%20opening%20at%20the%20neck.> accessed Apr. 8, 2022 (Year: 2022).

Achilli et al., "Advances In The Formation, Use And Understanding Of Multi-cellular Spheroids", Expert Opinion On Biological Therapy, vol. 12, No. 10, Jul. 2012, pp. 1347-1360.

Brandrup et al., "Polymer Handbook", Fourth Edition, Wiley-Interscience Publication, , Permeability and diffusion data, 1999, 9 pages (Contributors; Preface).

Endo et al., "Gene transfection to spheroid culture system on micropatterned culture plate by polyplex nanomicelle: a novel platform of genetically-modified cell transplantation", Drug Deliv. and Transl. Res., 2012, vol. 2, p. 398-405.

Hsiao et al., "Effects of 3D Microwell Culture on Initial Fate Specification in Human Embryonic Stem Cells", Published in final edited form as AIChE J. vol. 60 No.4, Apr. 2014, pp. 1225-1235.

Huang et al., "Preparation of dense Ta-LLZO/MgO composite Li-ion solid electrolyte: Sintering, microstructure, performance and the role of MgO", Journal of Energy Chemistry, vol. 39, 2019, pp. 8-16.

International Search Report and Written Opinion of the International Searching Authority; PCT/US2021/059622 dated May 23, 2022, 11 pages; European Patent Office.

Junji Fukuda et al., "Hepatocyte Spheroid Arrays Inside Microwells Connected With Microchannels", Biomicrofluidics 5, 2011, pp. 10.

Lin et al., "La2Zr2O7 and MgO co-doped composite Li-Garnet solid electrolyte", Journal of Energy Chemistry, vol. 40, 2020, pp. 132-136.

Lonza Inc., "SeaPrep Agarose: An Ultralow Gelling, Soft Agarose", Available Online at <http://www.lonzabio.jp/catalog/pdf/pd/PD031.pdf>, 2007, pp. 1-4.

Martin et al., "Agarose And Methylcellulose Hydrogel Blends For Nerve Regeneration Applications", J. Neural Eng., vol. 5, 2008, pp. 221-231.

McMillan, "Shear stress in microfluidic devices" Darwin Microfludics internet article (Year: 2017).

Polyimide: Japan Polyimide and Aromatic Polymers Study Group, 2010, pp. 364-371 Table 2.

Yang et al., "An Agarose-Gel Based Method for Transporting Cell Lines", Current Chemical Genomics, vol. 3, Jan. 2009, pp. 50-53.

Zuidema et al., "Fabrication And Characterization Of Tunable Polysaccharide Hydrogel Blends For Neural Repair", Acta Biomaterialia, vol. 7, No. 4, Apr. 2011, pp. 1634-1643.

* cited by examiner

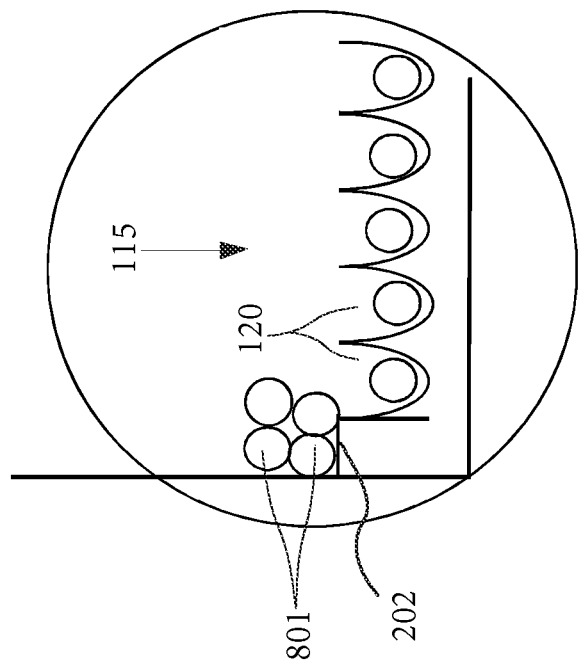
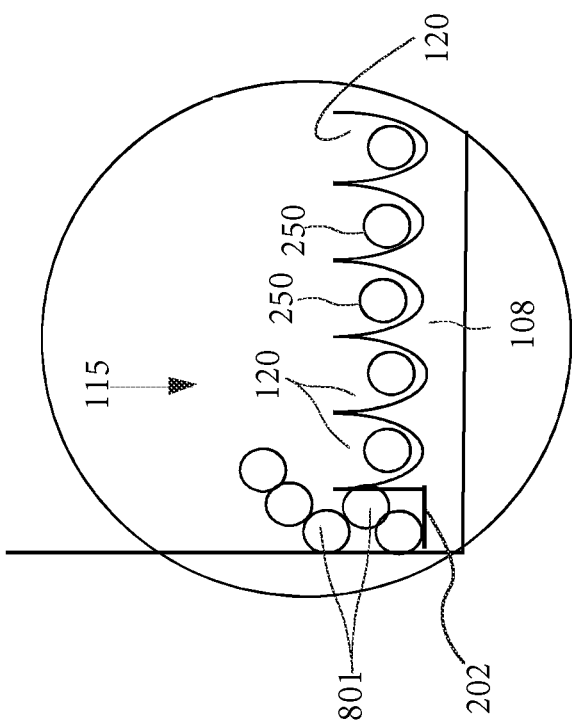
FIG. 2A
FIG. 2B

CELL CULTURE VESSEL FOR 3D CULTURE AND METHODS OF CULTURING 3D CELLS

CROSS REFERENCE TO RELATED APPLICATION

This is a national stage application under 35 U.S.C. § 371 of International Application No. PCT/US2018/042115 filed on Jul. 13, 2018, which claims the benefit of priority of U.S. Provisional Application Ser. No. 62/642,400 filed on Mar. 13, 2018, entitled "Cell Culture Container and Methods of Culturing Cells"; U.S. Provisional Application Ser. No. 62/532,639 filed on Jul. 14, 2017, entitled "Cell Culture Containers and Methods of Culturing Cells"; U.S. Provisional Application Ser. No. 62/532,648 filed on Jul. 14, 2017, entitled "Cell Culture Container and Methods of Culturing Cells"; and U.S. Provisional Application Ser. No. 62/532,671 filed on Jul. 14, 2017, entitled "Cell Culture Containers and Methods of Culturing Cells"; the content of which are relied upon and incorporated herein by reference in their entireties.

FIELD

The present disclosure relates generally to a cell culture vessel and methods of culturing cells, and more particularly, to a cell culture vessel for containing three-dimensional cells and methods of culturing three-dimensional cells in the cell culture vessel.

BACKGROUND

It is known to contain three-dimensional cells in a cell culture vessel. It is also known to culture three-dimensional cells in a cell culture vessel.

SUMMARY

The following presents a simplified summary of the disclosure in order to provide a basic understanding of some exemplary embodiments described in the detailed description.

In embodiments, the disclosure provides a cell culture vessel having microcavities, which may be present in an array, in a substrate, for culturing cells in three-dimensional conformation. In order to grow an array of cells growing in three-dimensional conformation, as spheroids or organoids, it is important to provide a substrate in a cell culture vessel that keeps all of the cells in microcavities. When cells grow in microcavities, they form spheroids, confined to a microcavity, and constrained in size. When cells escape from microcavities, or settle onto surfaces inside the cell culture vessel which are not structured and arranged to force the cells to grow in a desired three-dimensional conformation, cells will grow unconstrained. If cells in a cell culture vessel are able to grow unconstrained, they will form inhomogeneous populations of cells.

For some applications, it is desirable to grow and culture a homogeneous population of spheroids inside the cell culture vessel. For example, it is desirable to perform assays in a homogeneous population of cells to control for changes in cell physiology due to inconsistent cell morphology. And, when cellular therapeutics are the desired result of spheroid culture, homogenous cells are also desired to provide controlled, predictable therapeutic results.

When spheroids touch each other, they tend to conglomerate, forming large, non-uniform cellular structures. Cells can escape from microcavities during media changes, for example, when the flow of media into or out of the vessel creates turbulence and causes spheroids to escape the confines of microcavities. As a result, irregular cell agglomerates can form. The structure of the cell culture vessel is important in providing an array of microcavities chamber that constrain the cells to grow in the desired three-dimensional conformation without dislodging the spheroids from their microcavities and allowing them to form irregular cell structures. In embodiments, the disclosure provides a flange and a channel, forming a moat, which allow the vessel to be gently filled with media without creating undue turbulence.

When the interior of the cell culture vessel has flat surfaces, in addition to microcavities, cells can settle onto the flat surfaces and can grow into structures that are not uniform spheroids, but are non-uniform cellular structures. To ensure that cell culture vessels provide an environment that encourage the culture of uniform spheroids, in embodiments, cell culture vessels having reduced flat surfaces are provided. Moat structures, having an angled flange and a channel are provided as an outer perimeter of the substrate that surrounds the plurality of microcavities. And, these channel or moat structures have reduced flat surfaces in the cell culture area. In some embodiments, a method can include culturing cells in the cell culture vessel.

The above embodiments are exemplary and can be provided alone or in any combination with any one or more embodiments provided herein without departing from the scope of the disclosure. Moreover, it is to be understood that both the foregoing general description and the following detailed description present embodiments of the present disclosure, and are intended to provide an overview or framework for understanding the nature and character of the embodiments as they are described and claimed. The accompanying drawings are included to provide a further understanding of the embodiments, and are incorporated into and constitute a part of this specification. The drawings illustrate various embodiments of the disclosure, and together with the description, serve to explain the principles and operations thereof.

BRIEF DESCRIPTION OF THE DRAWINGS

These and other features, embodiments, and advantages of the present disclosure can be further understood when read with reference to the accompanying drawings in which:

FIGS. 2A and 2B are illustrations of two embodiments of an illustration of an enlarged area, shown as "2" in FIG. 1;

DETAILED DESCRIPTION

Figure 1:
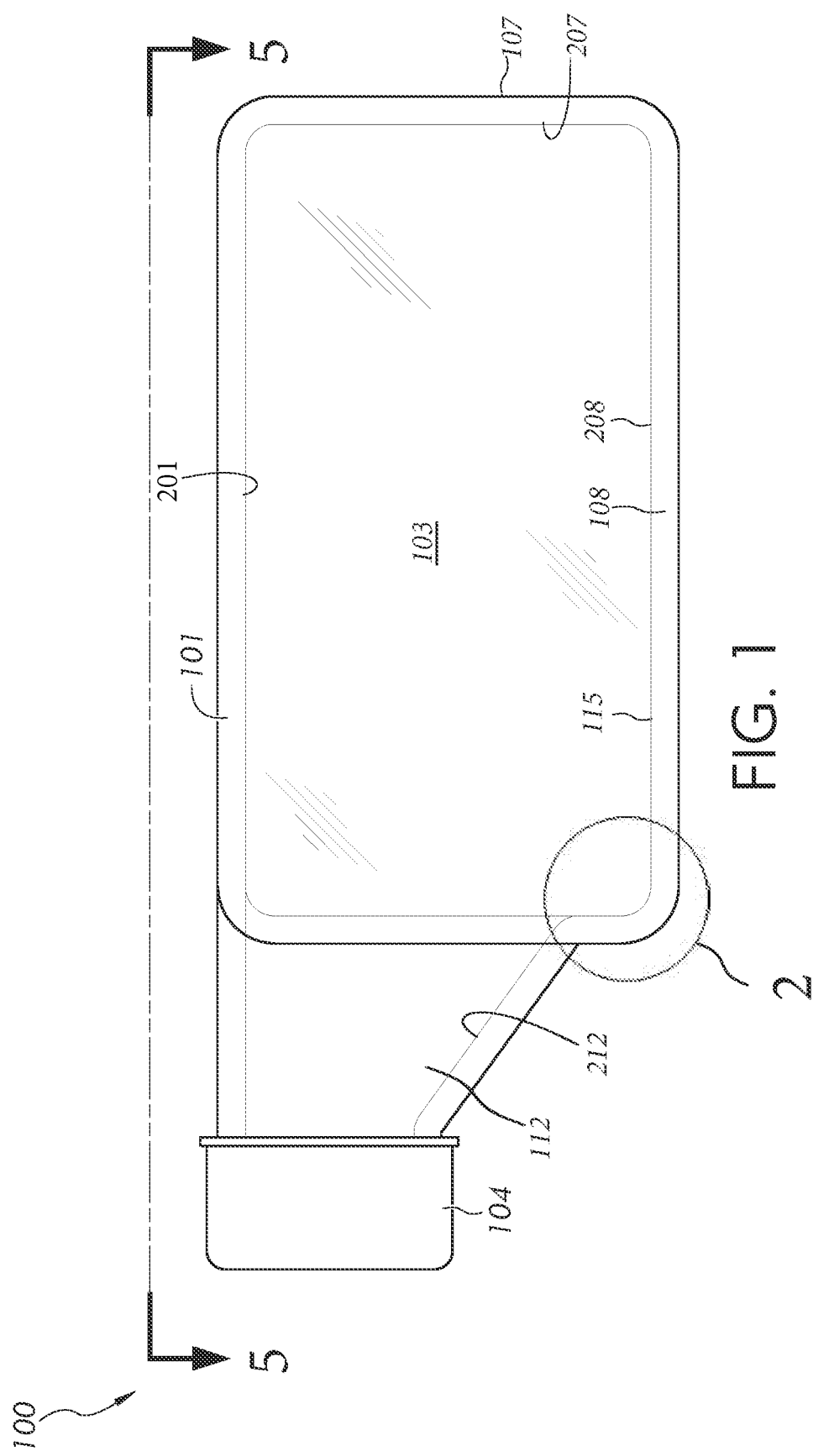
FIG. 1 schematically illustrates a side view of a first exemplary cell culture vessel in accordance with embodiments of the disclosure.

Features will now be described more fully hereinafter with reference to the accompanying drawings in which exemplary embodiments of the disclosure are shown. Whenever possible, the same reference numerals are used throughout the drawings to refer to the same or like parts. However, this disclosure can be embodied in many different forms and should not be construed as limited to the embodiments set forth herein.

A cell culture vessel (e.g., flask) can provide a sterile cell culture chamber for culturing cells. In some embodiments, culturing cells can provide information related to the study of diseases and toxicology, the efficacy of medications and treatments, characteristics of tumors, organisms, genetics, and other scientific, biological, and chemical principles of and relating to cells. The cell culture vessel can include a substrate including a plurality of microcavities (e.g., microcavities, micron-sized wells, submillimeter-sized wells) arranged, for example, in an array. The substrate can be placed in the flask or can form a portion of a boundary wall of the flask. That is, the substrate can be integral to the flask. For example, an array of microcavities can be formed in the bottom interior surface of a cell culture vessel. Or, a substrate having an array of microcavities can be inserted into a cell culture vessel and either rest on the bottom surface of the cell culture vessel or be affixed, by gluing, laser welding, ultrasonic welding, or some other method, to the bottom surface of the cell culture vessel. The substrate can include top and/or bottom sides that include undulating (e.g., sinusoidal) surfaces that form the plurality of microcavities. In some embodiments, the flask can be filled with a material (e.g., media, solid, liquid, gas) that facilitates growth of three-dimensional cell cultures (e.g., cell aggregates, spheroids). For example, a media including cells suspended in a liquid can be added to the cell culture chamber of the vessel. The suspended cells can collect in the plurality of microcavities and can form (e.g., grow) into groups or clusters of cells. These groups or clusters are spheroids or organoids.

For example, in some embodiments, a single spheroid can form in each microcavity of the plurality of microcavities based at least on gravity causing one or more cells suspended in a liquid to fall through the liquid and become deposited within each microcavity. The shape of the microcavity (e.g., a concave surface defining a well), and a surface coating of the microcavity that prevents the cells from attaching to the surface can also facilitate growth of three-dimensional cell cultures in each microcavity. That is, the cells form spheroids and are constrained by the dimensions of the microcavity to grow to a certain size. During culturing, the spheroids can consume media (e.g., food, nutrients) and produce metabolite (e.g., waste) as a byproduct. Thus, in some embodiments food media can be added to the cell culture chamber during culturing and waste media can be removed from the cell culture chamber during culturing. Attempts can be made when adding and removing media to avoid displacing the spheroids from the microcavities and promote desired cell culturing of the spheroids.

As compared to two-dimensional cell cultures, in some embodiments, three-dimensional cell cultures can produce multicellular structures that are more physiologically accurate and that more realistically represent an environment in which cells can exist and grow in real life applications as compared to simulated conditions in a laboratory. For example, three-dimensional cell cultures have been found to more closely provide a realistic environment simulating "in vivo" (i.e. within the living, in a real-life setting) cell growth; whereas two-dimensional cell-cultures have been found to provide an environment simulating "in vitro" (i.e., within the glass, in a laboratory setting) cell growth that is less representative of a real-life environment occurring outside of a laboratory. By interacting with and observing the properties and behavior of three-dimensional cell cultures, advancements in the understanding of cells relating to, for example, the study of diseases and toxicology, the efficacy of medications and treatments, characteristics of tumors, organisms, genetics, and other scientific, biological, and chemical principles of and relating to cells can be achieved.

Embodiments of an exemplary cell culture vessel 100 and methods of culturing cells in the exemplary cell culture vessel 100 are described with reference to FIG. 1-15. For example, FIG. 1 schematically illustrates a side view of a cell culture vessel 100 having a top 101, a bottom 108, and endwall 107, a neck 112 and an opening or aperture 105 shown in FIG. 1 covered by a cap 104. Each of the top 101, the bottom 108, the endwall 107 and the neck have interior surfaces. That is, the top 101 has an interior surface 201, the bottom has an interior surface 208, the neck 112 has an interior surface 212, the endwall 107 has an interior surface 207. The cell culture chamber 103 is that area of the vessel contained inside the interior surfaces of the vessel. In embodiments, the interior surface 208 of the bottom 108 has an array of microcavities 115.

FIG. 2A and FIG. 2B are schematic drawings of the area shown by circle "2" of FIG. 1. FIGS. 2A and 2B illustrate control vessels which result inhomogeneous cell culture. For example, if there are areas in the cell culture chamber 103, where cells may settle, where there are flat surfaces 202, cells 250 can congregate on flat surfaces instead of settling in the microcavities 120, and the cells can form irregular cellular conglomerates 801. For example, if there is a frame around the periphery of the array of microcavities, where the substrate comprising the array of microcavities attaches to the walls of the cell culture chamber 103 that is a flat ledge, cells may settle on the flat surfaces instead of settling into microcavities 120 as they fall through the media and settle on a surface. Examples of these uncontained irregular cellular conglomerates 801 are shown schematically in FIG. 2A and FIG. 2B. These cells can also invade neighboring microcavities and disrupt the culture of spheroids 250 contained in microcavities 120. In contrast, cells contained in microcavities 120 form regular, homogeneous spheroids 250 (see FIG. 18B, for example).

Figure 3A:
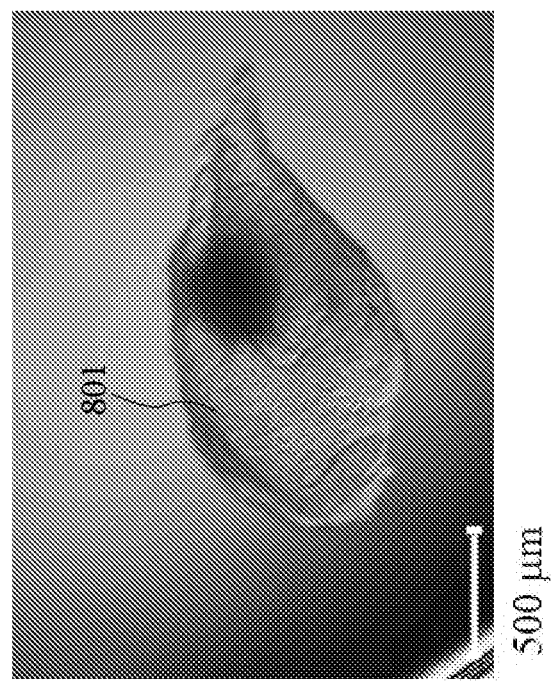
FIGS. 3A and 3B are photographs of the conformation of cells grown on the flat structures shown in FIG. 2A and FIG. 2B.
Figure 3B:
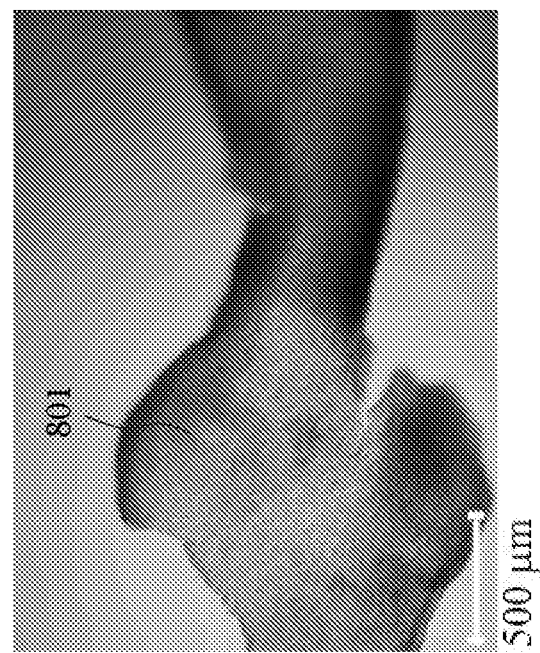

FIGS. 3A and 3B are photographs of irregular cellular conglomerations that formed on flat portions of cell culture vessels where these flat portions were present, according to Example 1, discussed below.

Turning back to FIG. 1, in some embodiments, the vessel 100 can include a cap 104 oriented to cover the aperture 105 to at least one of seal and block the aperture 105, thereby obstructing a path into the cell culture chamber 103 from outside the vessel 100 through the aperture 105. For clarity purposes, the cap 104 is removed and, therefore, not shown in other drawing figures, although it is to be understood that the cap 104 can be provided and selectively added to or removed from the aperture 105 of the vessel 100, in some embodiments, without departing from the scope of the disclosure. In some embodiments, the cap 204 can include a filter that permits the transfer of gas in to and/or out of the cell culture chamber 103 of the vessel 100. For example, in some embodiments, the cap 104 can include a gas-permeable filter oriented to regulate a pressure of gas within the cell culture chamber 103, thereby preventing pressurization (e.g., over-pressurization) of the cell culture chamber 103 relative to a pressure of the environment (e.g., atmosphere) outside the vessel 100.

Figure 4:
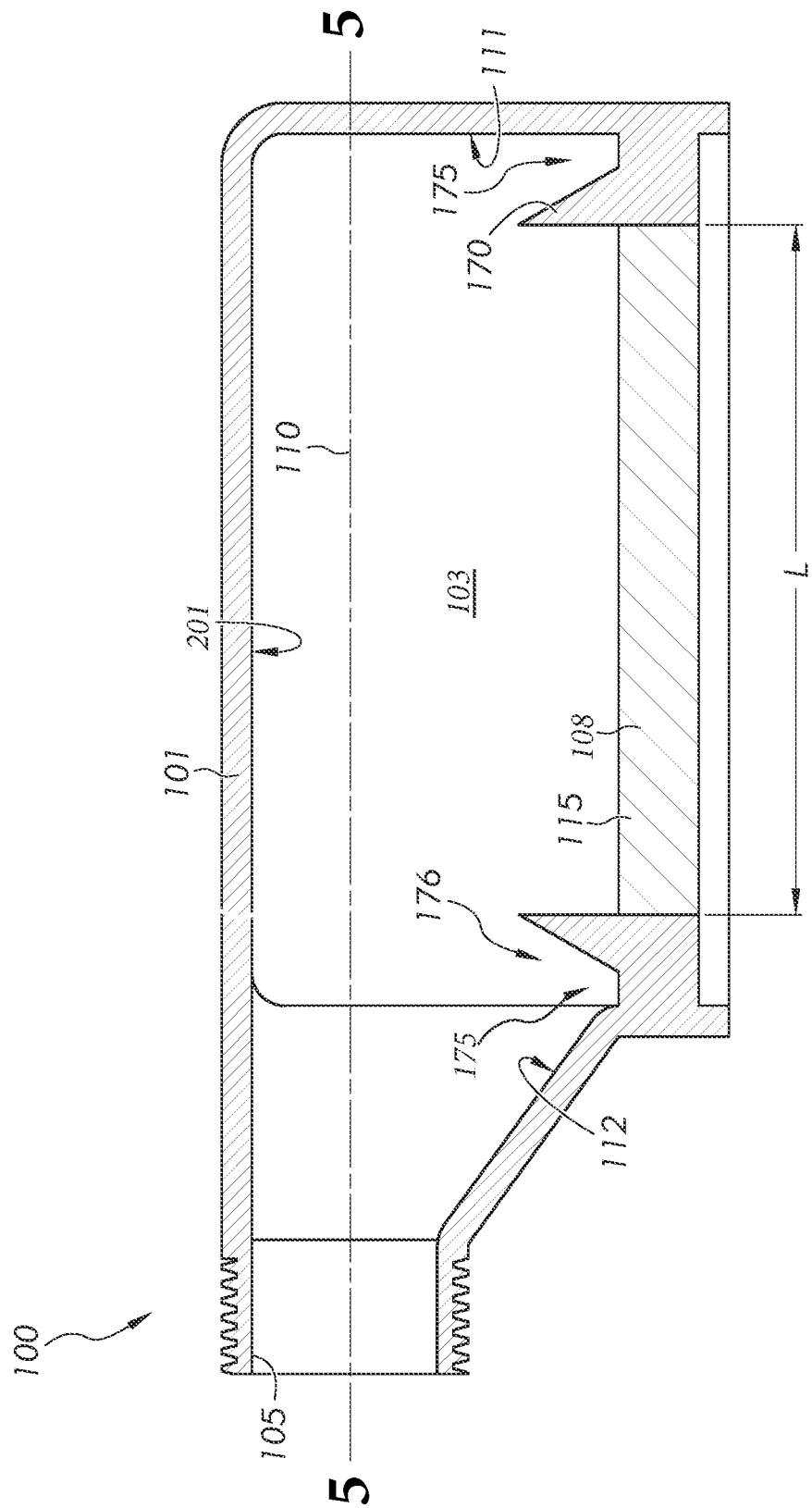
FIG. 4 shows an embodiment of the cross-sectional view of the cell culture vessel of FIG. 1 including a flange and a channel in accordance with embodiments of the disclosure.
Figure 5:
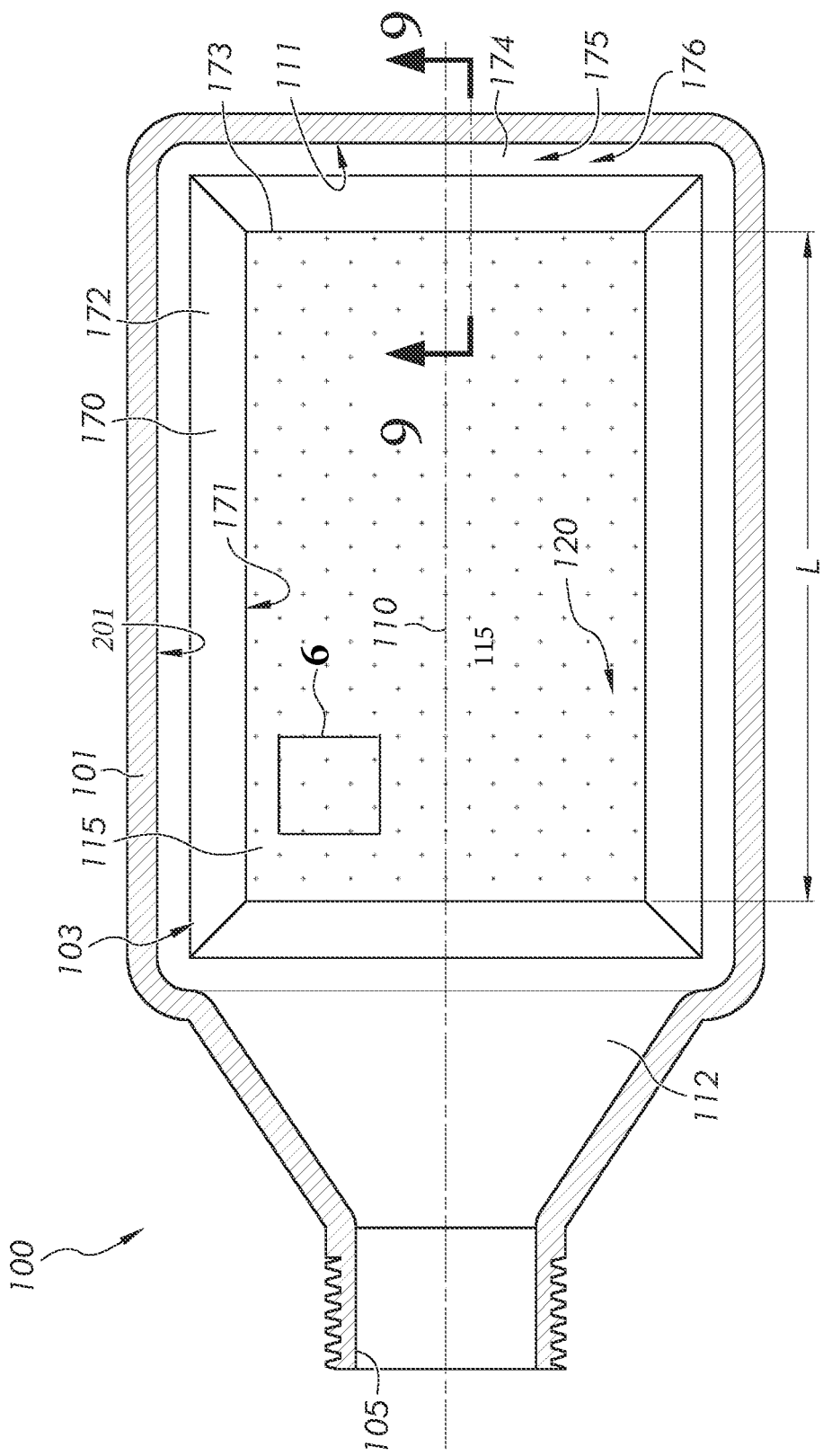
FIG. 5 shows an embodiment of the cross-sectional view of cell culture vessel of FIG. 1 taken at line 5-5 including a flange and a channel in accordance with embodiments of the disclosure.

As shown in FIG. 4, and in FIG. 5, which shows an alternate cross-sectional view along line 5-5 of FIG. 4, in some embodiments, the cell culture vessel 100 can include a flange 170 surrounding at least a portion of the array of microcavities 115. In FIG. 4 and FIG. 5, the array of microcavities 115 (also referred to as "substrate") is made up of individual microcavities 120 (see FIG. 6-8). Therefore, unless otherwise noted, it is to be understood that, in embodiments, substrate 115 can include one or more features of the microcavities 120a, 120b, 120c (See FIG. 6-8). Additionally, in embodiments, the cell culture vessel 100 can include a channel 175 surrounding at least a portion of the flange 170. Channel 175 has an opening 176. As shown in FIG. 5, in some embodiments, the flange 170 can surround all the microcavities of the array of microcavities 115. However, in some embodiments, the flange 170 can surround less than all (e.g., at least a portion of) the microcavities of the plurality of microcavities 120. Likewise, in some embodiments, the opening 176 of the channel 175 can surround the entire flange 170; however, in some embodiments, the opening 176 of the channel 175 can surround less than the entire flange 170 (e.g., at least a portion of) the flange 170. That is, the channel 175 may be closed in some areas, in embodiments. In some embodiments, the flange 170 and/or the channel 175 can be formed (e.g., manufactured) as an integral component of cell culture vessel 100. Alternatively, in some embodiments, the flange 170 and/or the channel 175 can be provided as a separate component that can be attached to the cell culture vessel 100 to, for example, retrofit an existing cell culture vessel, thereby providing the existing cell culture vessel with one or more features of the flange 170 and the channel 175 in accordance with embodiments of the disclosure. In embodiments, the array of microcavities 115 is integral to the interior surface 208 of the bottom 108 of the vessel. As shown in FIG. 4, the array of microcavities may be provided by an insert, a separate material introduced to or affixed into the flask. For example, a substrate having an array of microcavities 115 can be inserted into a cell culture vessel 100 and either rest on the bottom surface of the cell culture vessel or be affixed, by gluing, laser welding, ultrasonic welding, or some other method, to the bottom surface of the cell culture vessel.

FIG. 5 is a top-down view of the vessel, in embodiments. FIG. 5 illustrates that, in embodiments, the flange 170 surrounds the microcavity array 115, and the channel 175 surrounds the flange 170.

Figure 6:
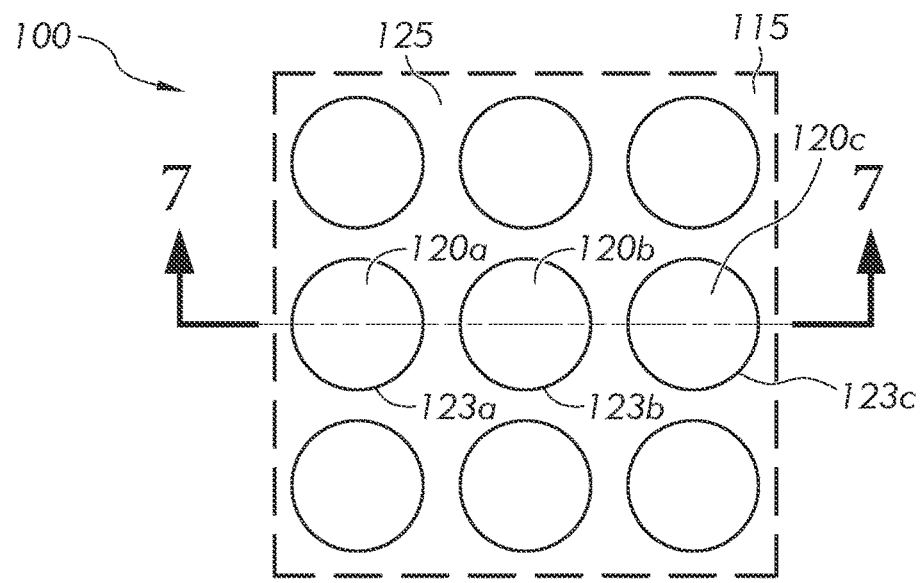
FIG. 6 illustrates an enlarged schematic representation of a portion of the cell culture vessel taken at view 6 of FIG. 5 showing a substrate having a plurality of microcavities in accordance with embodiments of the disclosure.
Figure 7:
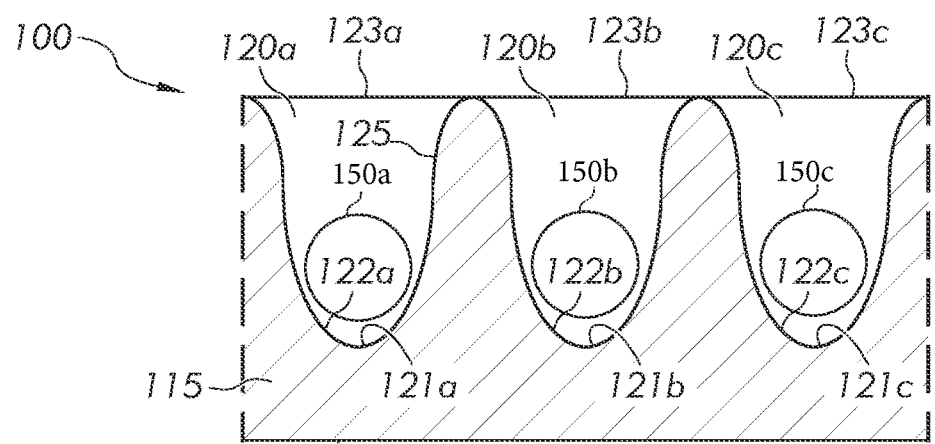
FIG. 7 shows a cross-sectional view of a portion of the cell culture vessel showing a substrate having a plurality of microcavities of FIG. 6 in accordance with embodiments of the disclosure.
Figure 8:
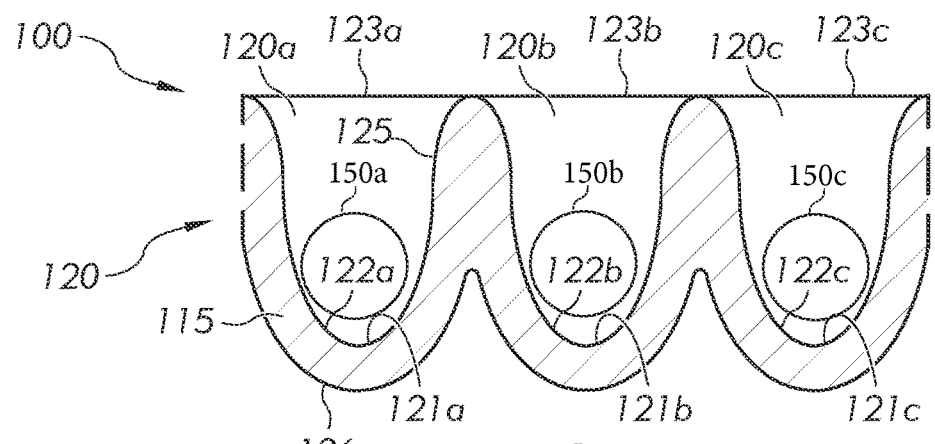
FIG. 8 shows an alternative exemplary embodiment of the cross-sectional view of the portion of the cell culture vessel having a plurality of microcavities of FIG. 6 in accordance with embodiments of the disclosure.

FIG. 6-8 show an enlarged schematic representation of a portion of the cell culture vessel taken at view 6 of FIG. 5, from a top-down perspective and from a cross-sectional perspective along line 7 of FIG. 6 (FIG. 7 and FIG. 8) showing a substrate having a plurality of microcavities 120 in accordance with embodiments of the disclosure. As shown in FIG. 6-8, in some embodiments, each microcavity 120a, 120b, 120c of the plurality of microcavities 120 can include a concave surface 121a, 121b, 121c (See FIG. 7 and FIG. 8) defining a well 122a, 122b, 122c. Further, each microcavity 120a, 120b, 120c can include an opening 123a, 123b, 123c (e.g., in a first side 125 of the substrate 115) to allow liquid and cells to enter the microwells t 122a, 122b, 122c. As shown in FIG. 7, in some embodiments, the first side 125 of the substrate 115 can include a non-linear (e.g., undulating, sinusoidal) profile and a second side 126 of the substrate 115 can include a planar (e.g., flat) profile. Similarly, as shown in FIG. 8, in some embodiments, both the first side 125 and the second side 126 of the substrate 115 can include a non-planar (e.g., undulating, sinusoidal) profile.

Comparing the substrate 115 shown in FIG. 7, where the first side 125 of the substrate 115 includes a non-linear (e.g., undulating, sinusoidal) profile and the second side 126 of the substrate 115 includes a planar (e.g., flat) profile, to the substrate 115 shown in FIG. 8, where both the first side 125 and the second side 126 of the substrate 115 include a non-planar (e.g., undulating, sinusoidal) profile, it can be seen that, in some embodiments, a thickness of the substrate 115, where both the first side 125 and the second side 126 of the substrate 115 include a non-planar (e.g., undulating, sinusoidal) profile, can be reduced. Thus, in some embodiments, providing both the first side 125 and the second side 126 of the substrate 115 with a non-planar (e.g., undulating, sinusoidal) profile (FIG. 8) can reduce the amount of material used to make the substrate 115 and can provide a substrate having a microcavity array 115 that includes thinner walled microcavities 120a, 120b, 120c than, for example, a substrate having a microcavity array 115, where the first side 125 of the substrate 115 includes a non-linear (e.g., undulating, sinusoidal) profile and the second side 126 of the substrate 115 includes a planar (e.g., flat) profile (FIG. 7). In some embodiments, thinner walled microcavities 120a, 120b, 120c can permit a higher rate of gas transfer (e.g., permeability) of the substrate to provide more gas in to and out of the well 122a, 122b, 122c during cell culturing. Thus, in some embodiments, providing both the first side 125 and the second side 126 of the substrate 115 with a non-planar (e.g., undulating, sinusoidal) profile (FIG. 8) can provide a healthier cell culture environment, thereby improving the culturing of cells in the microcavities 120a, 120b, 120c.

In some embodiments, the substrate 115 can include a polymeric material including, but not limited to, polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers. Additionally, in some embodiments, at least a portion of the well 122a, 122b, 122c defined by the concave surface 121a, 121b, 121c can be coated with an ultra-low binding material, thereby making the at least a portion of the well 122a, 122b, 122c non-adherent to cells. For example, in some embodiments, one or more of perfluorinated polymers, olefins, agarose, non-ionic hydrogels such as polyacrylamides, polyethers such as polyethyleneoxide, polyols such as polyvinylalcohol or mixtures thereof can be applied to at least a portion of the well 122a, 122b, 122c defined by the concave surface 121a, 121b, 121c.

Moreover, in some embodiments, each microcavity 120a, 120b, 120c of the plurality of microcavities 120 can include a variety of features and variations of those features without departing from the scope of the disclosure. For example, in some embodiments the plurality of microcavities 120 can be arranged in an array including a linear array (shown), a diagonal array, a rectangular array, a circular array, a radial array, a hexagonal close-packed arrangement, etc. Additionally, in some embodiments, the opening 123a, 123b, 123c can include a variety of shapes. In some embodiments, the opening 123a, 123b, 123c can include one or more of a circle, an oval, a rectangle, a quadrilateral, a hexagon, and other polygonal shapes. Additionally, in some embodiments, the opening 123a, 123b, 123c can include a dimension (e.g., diameter, width, diagonal of a square or rectangle, etc.) from about 100 microns (μm) to about 5000 μm. For example, in some embodiments, the opening 123a, 123b, 123c can include a dimension of 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, 1500 μm, 2000 μm, 2500 μm, 3000 μm, 3500 μm, 4000 μm, 4500 μm, 5000 μm, and any dimension or ranges of dimensions encompassed within the range of from about 100 μm to about 5000 μm.

In some embodiments, the well 122a, 122b, 122c defined by the concave surface 121a, 121b, 121c can include a variety of shapes. In some embodiments, the well 122a, 122b, 122c defined by the concave surface 121a, 121b, 121c can include one or more of a circular, elliptical, parabolic, hyperbolic, chevron, sloped, or other cross-sectional profile shape. Additionally, in some embodiments, a depth of the well 122a, 122b, 122c (e.g., depth from a plane defined by the opening 123a, 123b, 123c to the concave surface 121a, 121b, 121c can include a dimension from about 100 microns (μm) to about 5000 μm. For example, in some embodiments, the depth of the well 122a, 122b, 122c can include a dimension of 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, 1500 μm, 2000 μm, 2500 μm, 3000 μm, 3500 μm, 4000 μm, 4500 μm, 5000 μm, any dimension or ranges of dimensions encompassed within the range of from about 100 μm to about 5000 μm.

In some embodiments, three-dimensional cells 150 (e.g., spheroids, organoids 150a, 150b, 150c) that can be cultured in at least one microcavity 120a, 120b, 120c of the plurality of microcavities 120 can include a dimension (e.g., diameter) of from about 50 μm to about 5000 μm, and any dimension or ranges of dimensions encompassed within the range of from about 50 μm to about 5000 μm. In some embodiments, dimensions greater than or less than the explicit dimensions disclosed can be provided and, therefore, unless otherwise noted, dimensions greater than or less than the explicit dimensions disclosed are considered to be within the scope of the disclosure. For example, in some embodiments, one or more dimensions of the opening 123a, 123b, 123c, the depth of the well 122a, 122b, 122c, and the dimension of the three-dimensional cells 150 (e.g., spheroids 150a, 150b, 150c) can be greater than or less than the explicit dimensions disclosed without departing from the scope of the disclosure.

Figure 9:
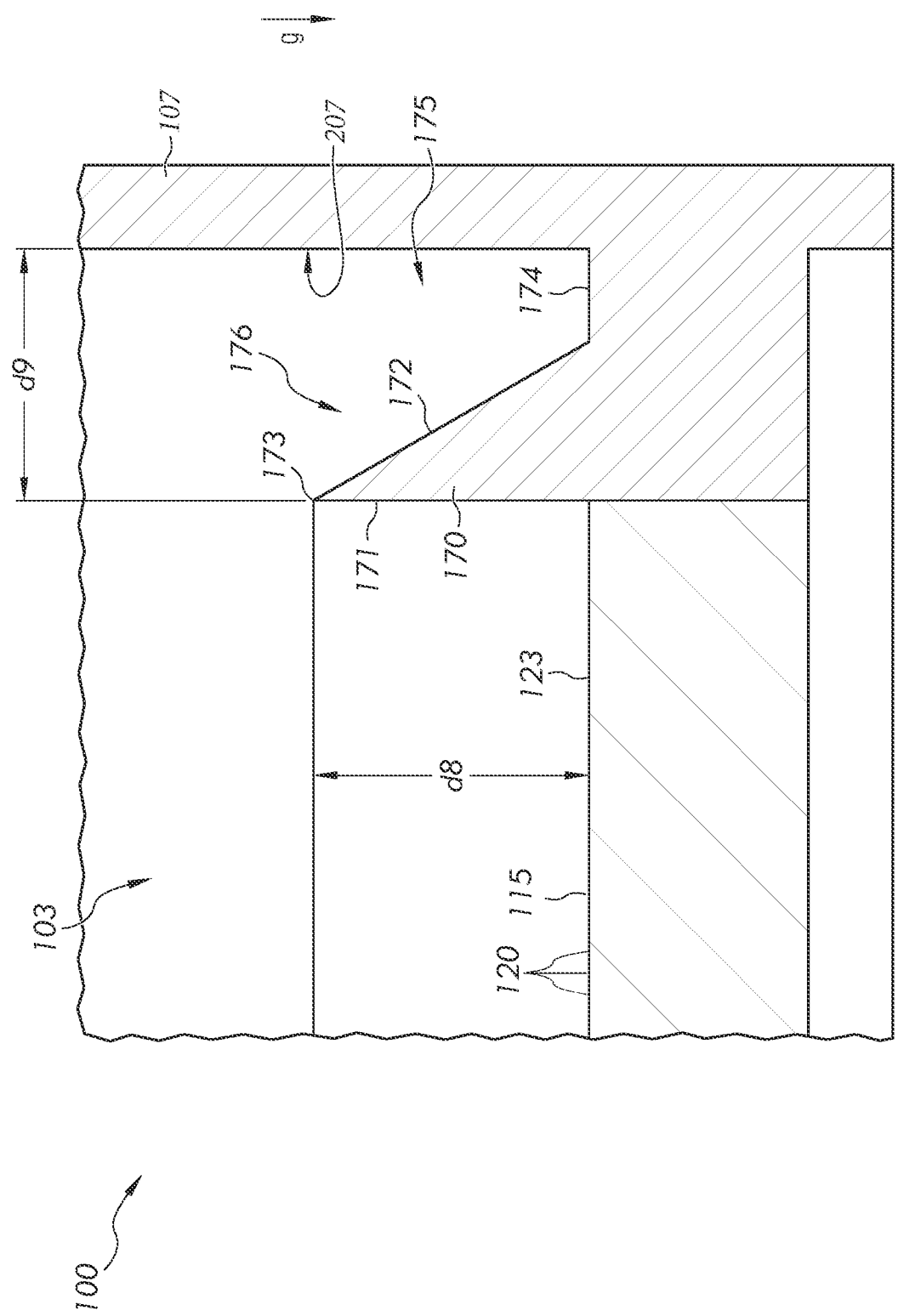
FIG. 9 shows an enlarged view of the area "9" shown in FIG. 4, in accordance with embodiments of the disclosure.

The enlarged view of the cell culture vessel 100 at area "9" of FIG. 4 including exemplary portions of the flange 170 and the channel 175, are shown in FIG. 9. For example, in some embodiments, the flange 170 can include an inner face 171 extending from the substrate 115 in a direction away from the concave surface 121a, 121b, 121c (See FIG. 6-8) of each microcavity 120a, 120b, 120c of the plurality of microcavities 120 to a perimeter 173 of the opening 176 of the channel 175. Turning back to FIG. 5, in some embodiments, the inner face 171 can surround all the microcavities of the plurality of microcavities 120; however, in some embodiments, the inner face 171 can surround less than all (e.g., at least a portion of) the microcavities of the plurality of microcavities 120. Likewise, in some embodiments, the opening 176 of the channel 175 can surround the entire inner face 171; however, in some embodiments, the opening 176 of the channel 175 can surround less than the entire (e.g., at least a portion of) the inner face 171.

As shown in FIG. 9, in some embodiments, the perimeter 173 of the opening 176 of the channel 175 can be spaced a distance "d8" from the portion 123 of the substrate 115 in a direction away from the concave surface 121a, 121b, 121c (See FIG. 6-8) of each microcavity 120a, 120b, 120c of the plurality of microcavities 120. In some embodiments, the distance "d8" can be within a range of from about 2 millimeters (mm) to about 8 mm, for example, from about 4 mm to about 8 mm, although other values, (e.g., less than 2 mm or greater than 8 mm) can be provided in other embodiments without departing from the scope of the disclosure. Additionally, in some embodiments, the perimeter 173 of the opening 176 of the channel 175 can be spaced a distance "d9" from the inner surface 102 of the wall 101 in a direction toward the portion 123 of the substrate 115. Thus, in some embodiments, the opening 176 of the channel 175 can be defined between the inner surface 207 of the endwall 107 and the perimeter 173. In some embodiments, the channel 175 can include an outer face 172 extending from the perimeter 173 of the opening 176 of the channel 175 in a direction toward the concave surface 121a, 121b, 121c (See FIG. 6-8) of each microcavity 120a, 120b, 120c of the plurality of microcavities 120 to a base 174 of the channel 175. As shown in FIG. 5, in some embodiments, the outer face 172 can surround all the microcavities of the plurality of microcavities 120; however, in some embodiments, the outer face 172 can surround less than all (e.g., at least a portion of) the microcavities of the plurality of microcavities 120. Likewise, in some embodiments, the base 174 of the channel 175 can surround the entire outer face 172; however, in some embodiments, the base 174 of the channel 175 can surround less than the entire (e.g., at least a portion of) the outer face 172.

Figure 10:
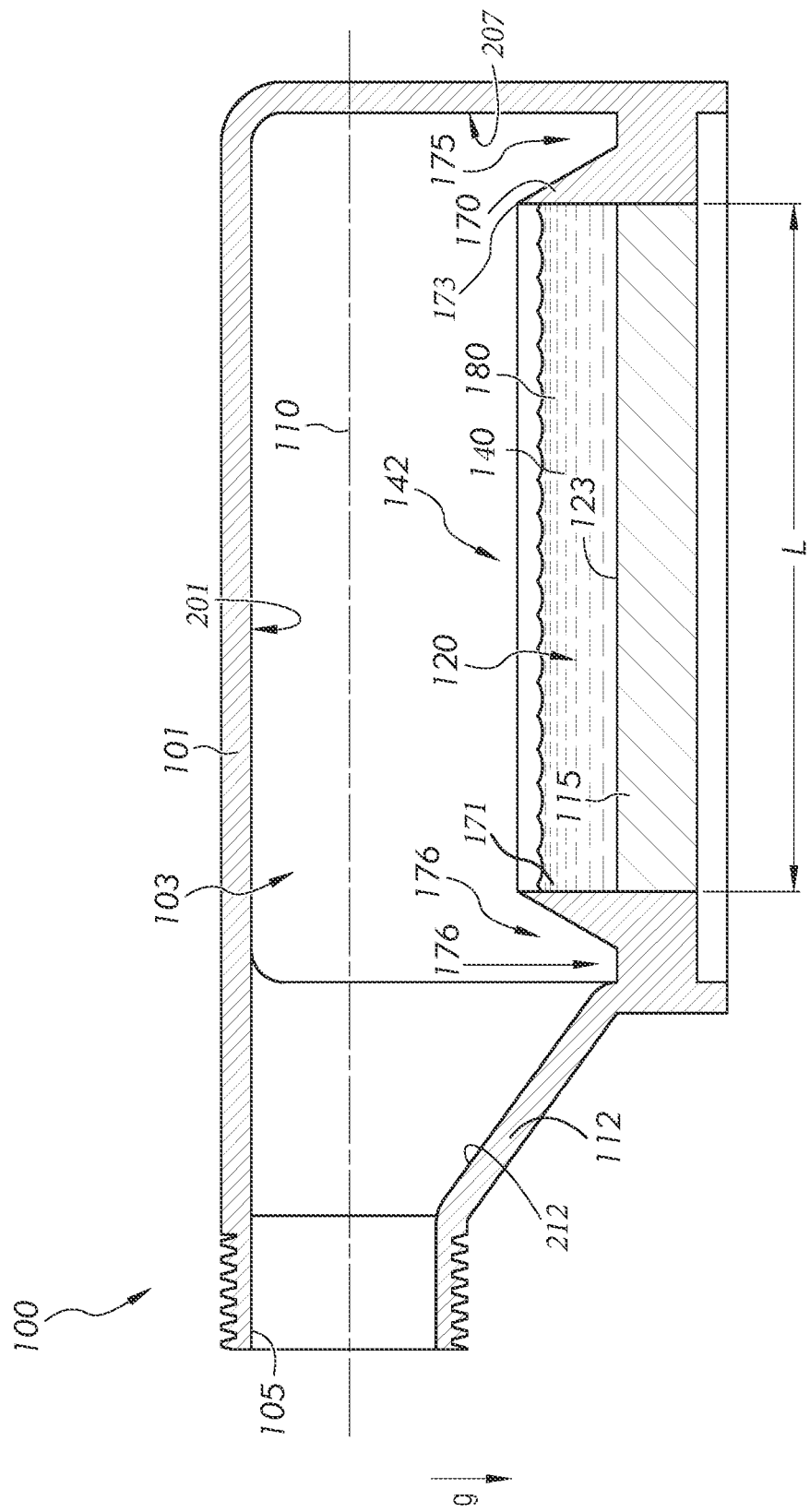
FIG. 10 shows an embodiment of the cell culture vessel of FIG. 4 including a method of culturing cells in the first exemplary cell culture vessel in accordance with embodiments of the disclosure.

A method of culturing cells in the cell culture vessel 100 including the flange 170 and the channel 175 will now be described with reference to FIG. 10-17. For example, as shown in FIG. 10, in some embodiments, the method can include containing a predetermined amount of liquid 180 in a region 142 of the cell culture chamber 103 without liquid of the predetermined amount of liquid 180 contacting the channel 175. In some embodiments, the region 142 can be defined based at least in part by the flange 170 and the substrate 115. For example, in some embodiments, the region 142 can be defined based at least in part by inner face 171 of the flange 170 and the portion 123 of the substrate 115. In some embodiments, preventing liquid of the predetermined amount of liquid 180 from contacting the channel 175, at this stage of the method, can provide several advantages that, for example, facilitate improved culturing of the cells 150. For example, in some embodiments, at least a portion of the predetermined amount of liquid 180 can include a culture solution or media including a liquid including solid particles (e.g., cells) suspended in the liquid. Accordingly, in some embodiments, the method can include depositing liquid 140 of the predetermined amount of liquid 180 (See FIG. 10) in at least one microcavity 120a, 120b, 120c of the plurality of microcavities 120 and culturing cells 150 (e.g., spheroids 150a, 150b, 150c) in the at least one microcavity 120a, 120b, 120c after depositing the liquid 140 in the at least one microcavity 120a, 120b, 120c. For illustrative purposes only, the structures of the array of microcavities 115 including the plurality of microcavities 120 are omitted from FIG. 10-17 with the understanding that, unless otherwise noted, in some embodiments, one or more features of the substrate 115 (See FIG. 6-8) can be provided alone or in combination with one or more features of the first exemplary cell culture vessel 100 without departing from the scope of the disclosure.

Turning back to FIG. 9, in some embodiments, the inner face 171 of the flange 170 can include a vertical orientation (e.g., extending substantially in the direction of gravity); however, in some embodiments, the inner face 171 can be inclined relative to the direction of gravity to, for example, direct cells toward the openings 123a, 123b, 123c of the microcavities 120a, 120b, 120c (See FIG. 6-8). Moreover, in some embodiments, the opening 123a of the microcavity 120a, for example, can be positioned to abut the inner face 171 of the flange 170. For example, in some embodiments, the opening 123a of the microcavity 120a can be flush with the inner face 171 of the flange 170 such that cells suspended in a liquid will fall (e.g., based at least on the force of gravity) and/or be directed by the inner face 171 into the reservoir 122a of the microcavity 120a without settling on or adhering to a surface of the vessel 100, including but not limited to the base 174 of the channel 175.

In some embodiments, cells that settle on or adhere to a surface of the vessel 100, including but not limited to the base 174 of the channel 175, can accumulate and grow (e.g., multiply) outside of the microcavities 120a, 120b, 120c causing problems with respect to desired growth of three-dimensional cells within the microcavities 120a, 120b, 120c. For example, in some embodiments, cells that do not fall (based at least on the force of gravity) into the reservoir 122a, 122b, 122c and that accumulate or attach to other surfaces of the vessel 100, including but not limited to the base 174 of the channel 175, can grow outside of the reservoir 122a, 122b, 122c and disrupt (e.g., discourage, alter, slow, or prevent) desired growth of three-dimensional cells within the reservoir 122a, 122b, 122c. Similarly, in some embodiments, cells that accumulate or attach to other surfaces of the vessel 100, including but not limited to the base 174 of the channel 175, can grow and dislodge three-dimensional cells in the reservoir 122a, 122b, 122c, thereby disrupting or destroying desired growth of three-dimensional cells within the reservoir 122a, 122b, 122c and altering desired size uniformity of the cells. Accordingly, in some embodiments, by containing the predetermined amount of liquid 180 in the region 142 of the cell culture chamber 103 without liquid of the predetermined amount of liquid 180 contacting the channel 175, all cells suspended within the liquid can be directed into the reservoirs 122a, 122b, 122c, thus reducing and eliminating problems that can otherwise occur if cells attach to surfaces of the vessel 100, outside the reservoirs 122a, 122b, 122c, including but not limited to the base 174 of the channel 175.

Accordingly, in some embodiments, the method can include depositing liquid 140 of the predetermined amount of liquid 180 (See FIG. 10) on the array of microcavities 115, surrounded by flange 170. In this way, at least one microcavity 120a, 120b, 120c of the plurality of microcavities 120 in the microcavity array 115 and culturing cells 150 (e.g., spheroids 150a, 150b, 150c, shown in FIGS. 7 and 8) in the at least one microcavity 120a, 120b, 120c after depositing the liquid 140 on the array of microcavities 115. Moreover, in some embodiments, during culturing, the spheroids 150a, 150b, 150c can consume media (e.g., food, nutrients) and produce metabolite (e.g., waste) as a byproduct. Thus, in some embodiments food media can be added to the cell culture chamber 103 during culturing and waste media can be removed from the cell culture chamber 103 during culturing. As discussed more fully below, in some embodiments, attempts can be made when adding and removing media to avoid displacing the spheroids 150a, 150b, 150c from the microcavities 120a, 120b, 120c and promote desired cell culturing of the spheroids 150a, 150b, 150c.

Moreover, in some embodiments, with respect to a unit area of the substrate 115 (e.g., a unit area providing a respective surface on which one or more cells can be cultured), three-dimensional cell culturing can consume more media (e.g., food, nutrients) and produce more media (e.g., waste) as a byproduct than, for example, a comparable two-dimensional cell culture. Thus, in some embodiments, as compared to, for example, a comparable two-dimensional cell culture, three-dimensional cell cultures in accordance with embodiments of the disclosure can include more frequent media exchanges (e.g., addition of food, nutrients and/or removal of waste) for a comparable period of time. In addition or alternatively, in some embodiments, as compared to, for example, a comparable two-dimensional cell culture, three-dimensional cell cultures in accordance with embodiments of the disclosure can include larger media volumes (e.g., consume more food, nutrients and/or produce more waste) for a comparable period of time. Accordingly, in some embodiments, as discussed more fully below, one or more features of the cell culture vessel 100 and the methods of culturing cells 150 in the cell culture vessel 100 can provide advantages with respect to the frequency of media exchanges as well as the volume of media that can be one or more of contained within the cell culture chamber 103 of the vessel 100, added to the cell culture chamber 103, and removed from the cell culture chamber 103, thereby providing a desirable, effective environment in which to culture three-dimensional cells.

Figure 11:
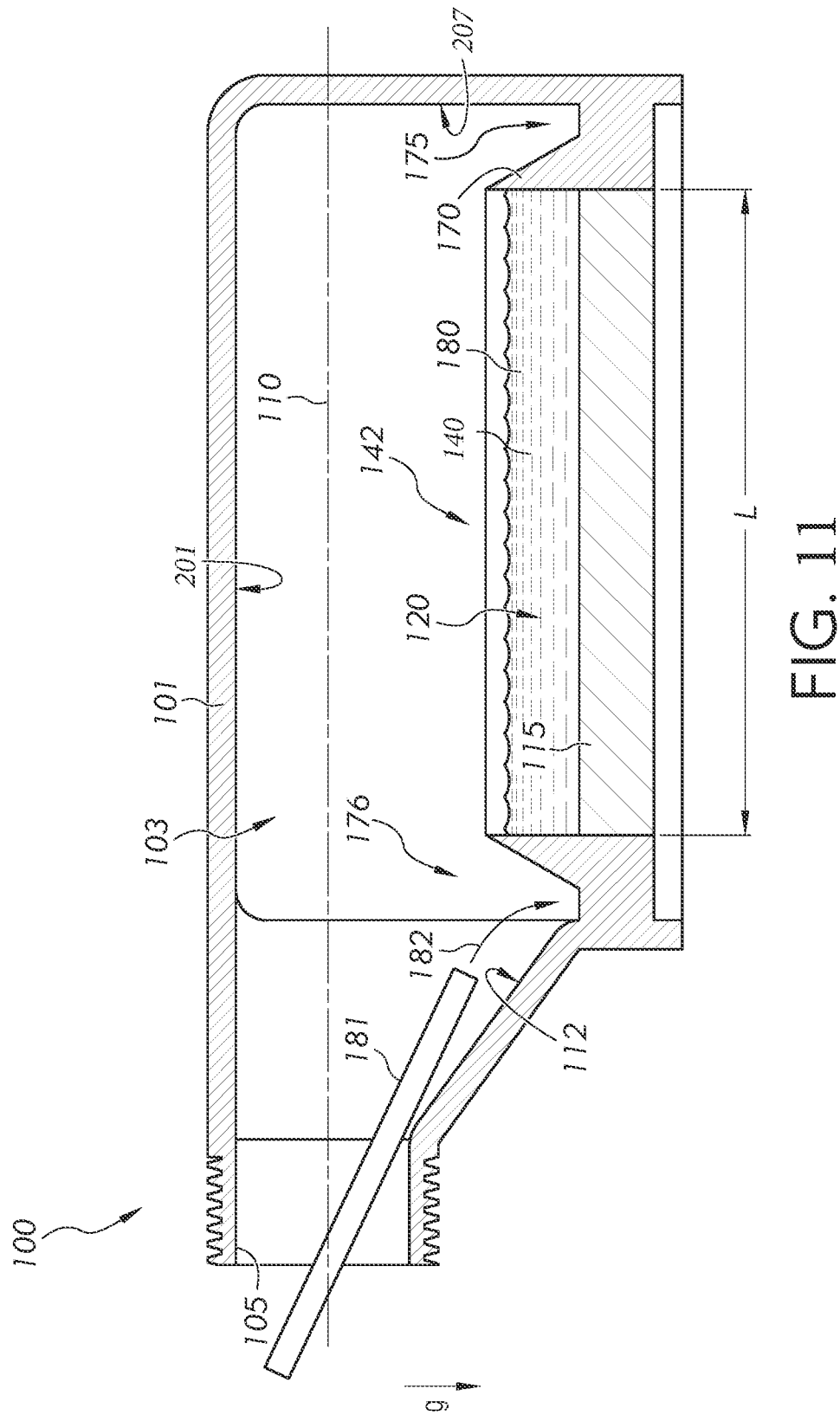
FIG. 11 shows an embodiment of the cell culture vessel of FIG. 4 including a method of adding material to the channel with a dispensing-port in accordance with embodiments of the disclosure.

For example, as shown in FIG. 11, in some embodiments, the method can include adding material (e.g., food, nutrients) from outside the vessel 100 into the cell culture chamber 103 by inserting a dispensing-port 181 into the aperture 105 and dispensing material 182 from the dispensing-port into the opening 176 of the channel 175. Additionally, in some embodiments, the method can include adding material (e.g., food, nutrients) from outside the vessel 100 into the cell culture chamber 103 by inserting a dispensing-port 181 into the aperture 105 and dispensing material 182 from the dispensing-port into the opening 176 of the channel 175 after containing the predetermined amount of liquid 180 in the region 142 of the cell culture chamber 103 without liquid of the predetermined amount of liquid 180 contacting the channel 175. Thus, in some embodiments, the method can include culturing cells 150 in at least one microcavity 120 while dispensing material 182 from the dispensing-port 181 into the opening 176 of the channel 175.

Figure 12:
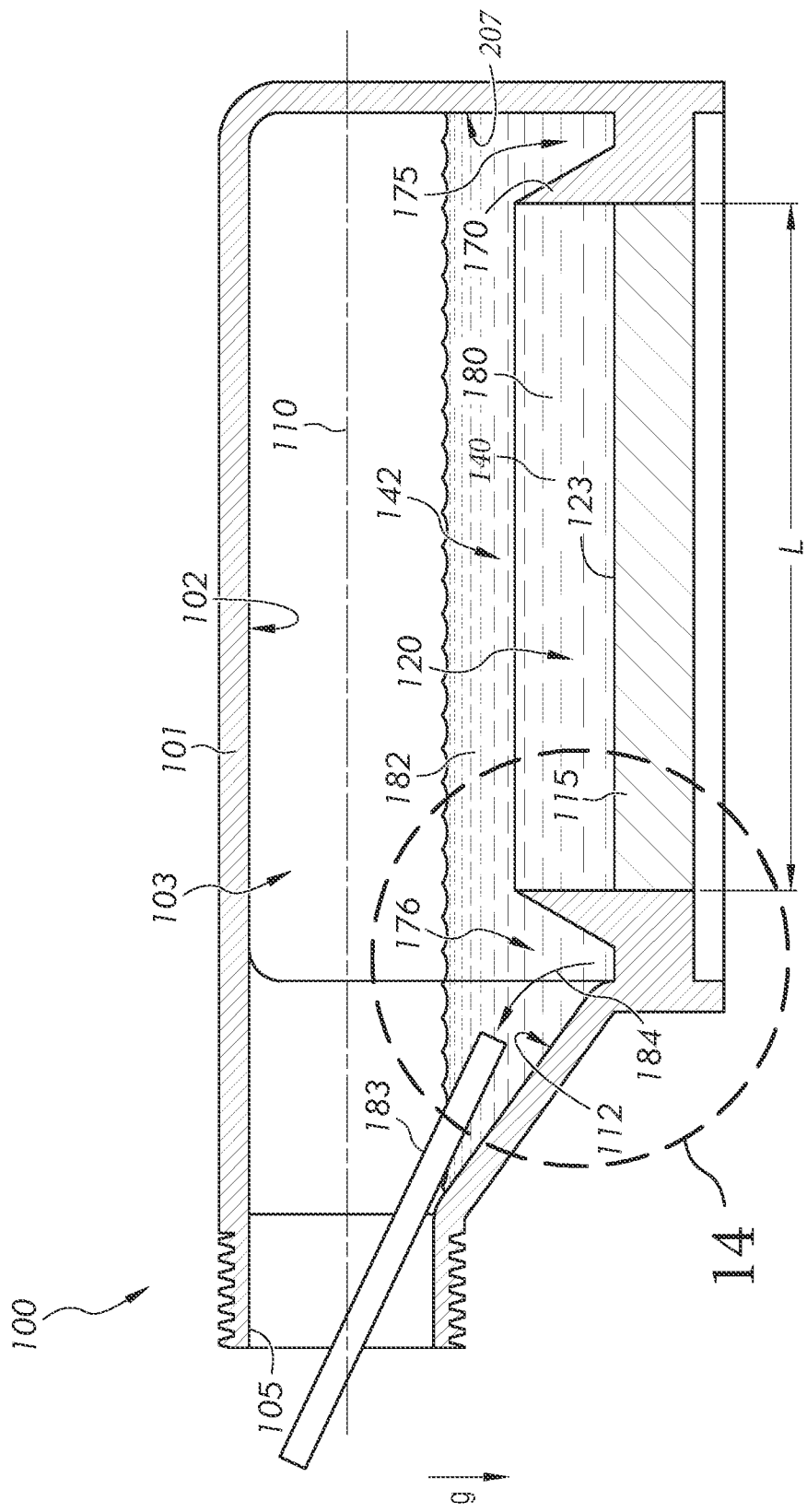
FIG. 12 shows an embodiment of the cell culture vessel of FIG. 4 including a method of removing material from the channel with a collecting-port in accordance with embodiments of the disclosure.

FIG. 12 schematically shows the material 182 added into the cell culture chamber 103 to, for example, provide the cells 150 included in the predetermined amount of liquid 180 with food media which the cells 150 can consume while being cultured. Likewise, as shown in FIG. 12, in some embodiments, the method can include removing material (e.g., waste) from the cell culture chamber 103 to outside the vessel 100 by inserting a collecting-port 183 into the aperture 105 and collecting material 184 from the channel 175 with the collecting-port 183. Additionally, in some embodiments, the method can include removing material (e.g., waste) from the cell culture chamber 103 by inserting the collecting-port 183 into the aperture 105 and collecting material 184 from the channel 175 with the collecting-port 183 after adding material (e.g., food, nutrients) into the cell culture chamber 103. Thus, in some embodiments, the method can include culturing cells 150 in at least one microcavity of the plurality of microcavities 120 (See FIGS. 7 and 8) while collecting material 184 from the channel 175 with the collecting-port 183.

Figure 13:
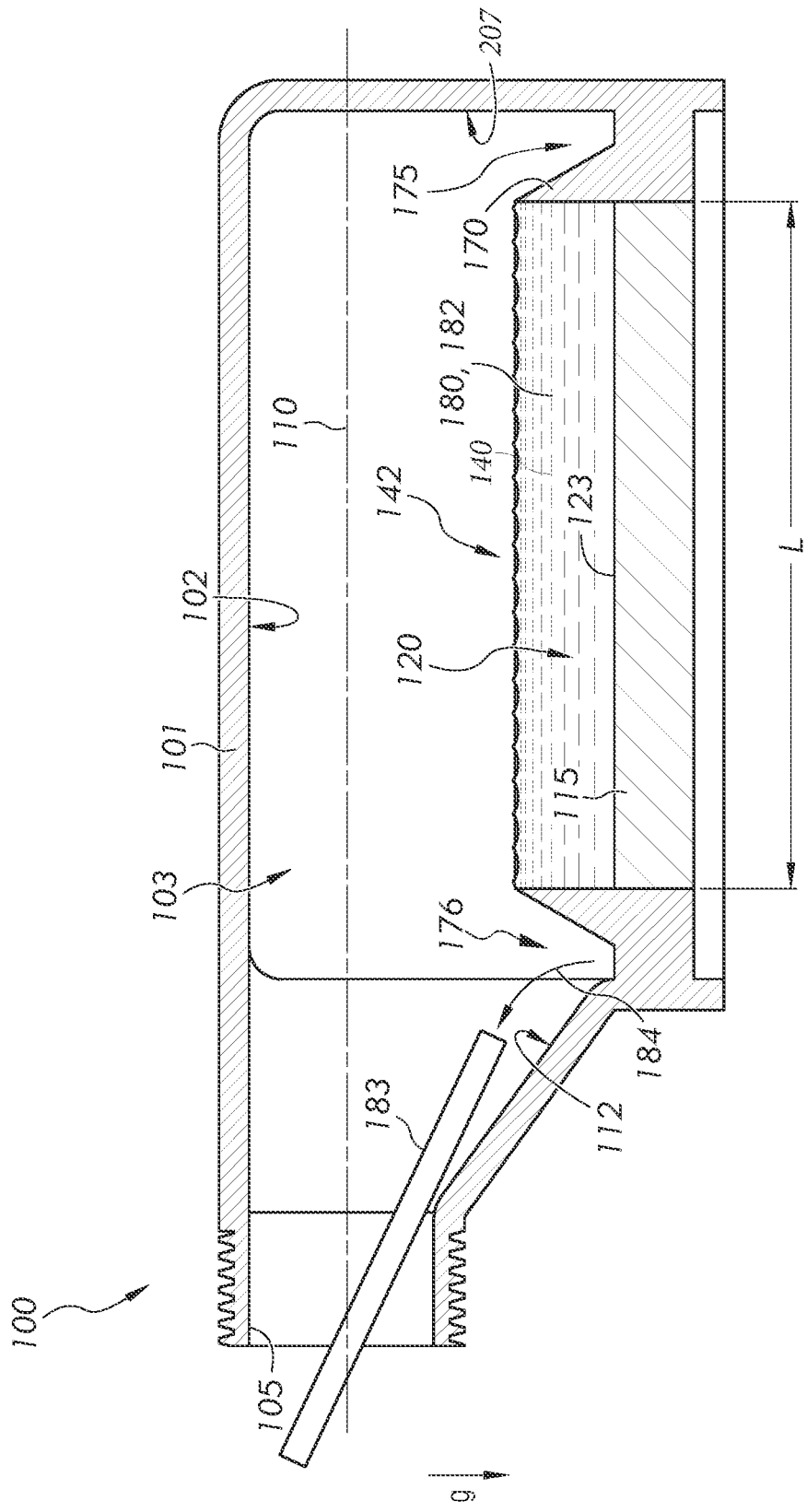
FIG. 13 shows a step of the method of removing material with a collecting-port from the channel of the cell culture vessel of FIG. 4 in accordance with embodiments of the disclosure.

FIG. 13 schematically shows material 184 removed from the cell culture chamber 103 to, for example, remove waste media, which the cells 150 can produce while being cultured, from the predetermined amount of liquid 180 and the material 182. For example, in some embodiments, during culturing, the cells 150 can consume all or some of the food media (e.g., material 182) added to the cell culture chamber 103 and produce (e.g., metabolize as a byproduct) all or some of the waste media (e.g., material 184) removed from the cell culture chamber 103. In some embodiments, while culturing cells 150 the methods of adding food media 182 to the cell culture chamber 103 (See FIG. 11 and FIG. 12) and removing waste media 184 from the cell culture chamber 103 (See FIG. 12 and FIG. 13) can provide a healthy environment in which the cells 150 can be cultured. For example, in some embodiments, methods in accordance with embodiments of the disclosure of adding food media 182 to the cell culture chamber 103 (See FIG. 11 and FIG. 12) and removing waste media 184 from the cell culture chamber 103 (See FIG. 12 and FIG. 13 can, at least in part, increase one or more of the quality, duration, and effectiveness of the cell culturing process as compared to a cell culture environment to which food media is not added or from which waste media is not removed. Likewise, in some embodiments, one or more features of the vessel 100 as well as methods in accordance with embodiments of the disclosure of adding food media 182 to the cell culture chamber 103 (See FIG. 11 and FIG. 12) and removing waste media 184 from the cell culture chamber 103 (See FIG. 12 and FIG. 13) can, at least in part, be performed more frequently and with greater effectiveness with respect to the volume of media that can be one or more of contained within the cell culture chamber 103 of the vessel 100, added to the cell culture chamber 103, and removed from the cell culture chamber 103 during the cell culturing process as compared to, for example, a cell culture vessel not including one or more features of the disclosure as well as methods not including one or more steps of the disclosure.

Additionally, in some embodiments, the method can include moving the vessel 100 and collecting the material 184 from the channel 175 with the collecting-port 183. For example, in some embodiments, moving the vessel 100 can include at least one of translating and rotating the vessel 100 from a first orientation (e.g., the orientation provided in FIG. 13) to a second orientation (e.g., the orientation provided in FIG. 14). In some embodiments, the first orientation (e.g., the orientation provided in FIG. 13) can provide the vessel 100 with the axis 110 extending substantially perpendicular relative to the direction of gravity "g" although other orientations of the axis 110 relative to the direction of gravity "g" can be provided in other embodiments to define the first orientation. Likewise, in some embodiments, the second orientation (e.g., the orientation provided in FIG. 14) can provide the vessel 100 with the axis 110 extending at an angle that is substantially non-perpendicular relative to the direction of gravity "g" although other orientations of the axis 110 relative to the direction of gravity "g" can be provided in other embodiments to define the second orientation.

In some embodiments, the first orientation can provide the axis 110 at a first angle relative to the direction of gravity "g" that is different than a second angle of the axis 110 relative to the direction of gravity "g" provided by the second orientation. Additionally, in some embodiments, the axis 110 of the vessel 100 can extend substantially perpendicular to the direction of gravity "g" while one or more of containing the predetermined amount of liquid 180 in the region 142 of the cell culture chamber 103 (See FIG. 10), while adding material 182 to the cell culture chamber 103 (See FIG. 11), and while removing material 184 from the cell culture chamber 103 (See FIG. 12 and FIG. 13). For example, in some embodiments, the vessel 100 can be placed on, for example, a horizontal surface (not shown) that defines a major surface perpendicular to the direction of gravity "g" with the axis 110 of the vessel 100 extending substantially parallel to the major surface of the horizontal surface (not shown) relative to the direction of gravity "g". In addition or alternatively, in some embodiments, the vessel 100 can be supported (e.g., held, suspended) by one or more structures (e.g., frame, mount, human hand, etc.) with the axis 110 extending substantially perpendicular to the direction of gravity "g". Likewise, in some embodiments, the vessel 100 can be supported (e.g., held, suspended) by one or more structures (e.g., frame, mount, human hand, etc.) with the axis 110 extending at an angle that is substantially non-perpendicular relative to the direction of gravity "g" as a result of, for example, moving the vessel 100 (See FIG. 14) before and/or while collecting the material 184 from the channel 175 with the collecting-port 183.

Figure 14:
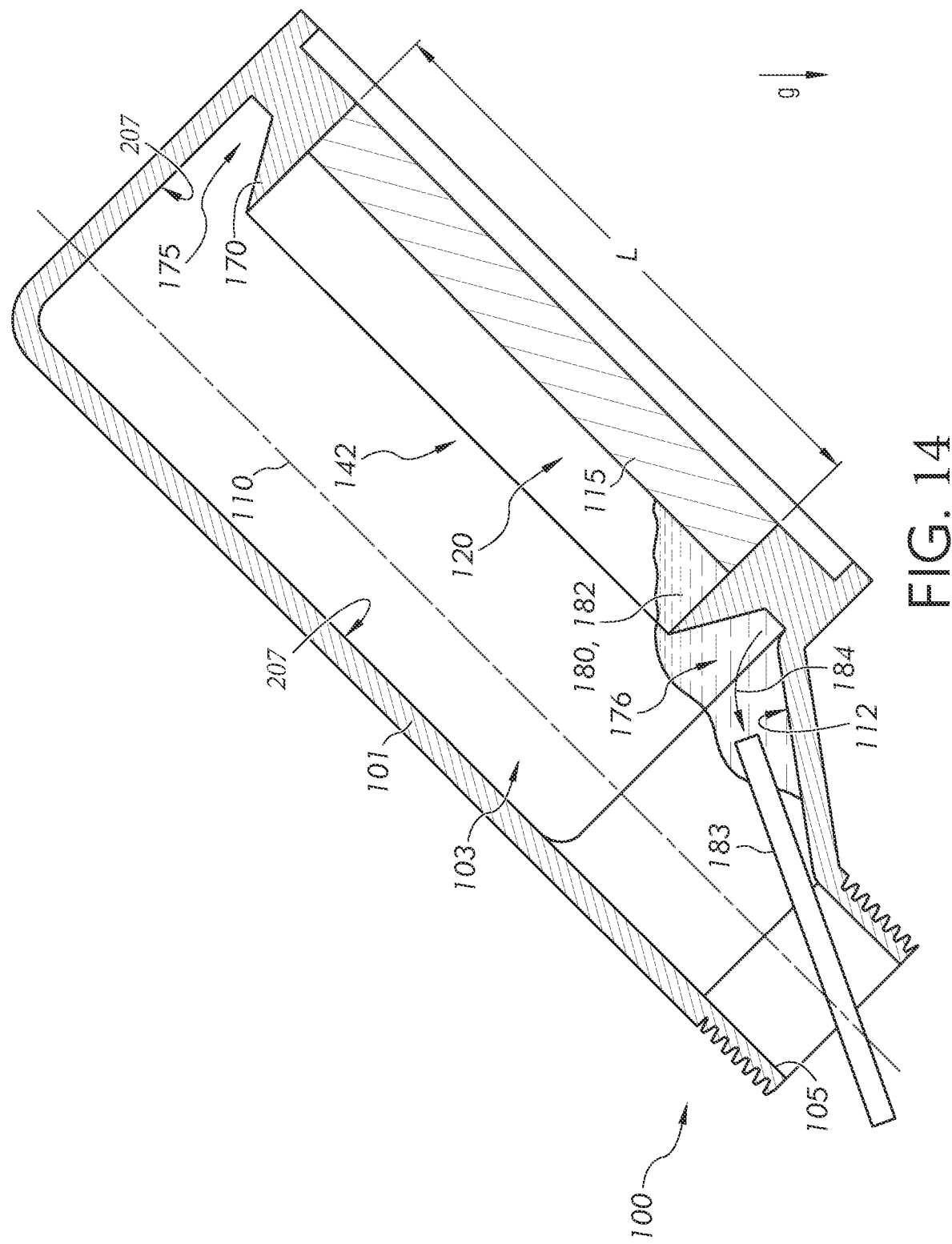
FIG. 14 shows a step of the method of removing material with a collecting-port from the channel of the cell culture vessel of FIG. 4 in accordance with embodiments of the disclosure.

Thus, as shown schematically in FIG. 14, in some embodiments, the method can include moving the vessel 100 to cause at least a portion of the predetermined amount of liquid 180 and the added material 182 (including waste material 184) to flow from the region 142 over the flange 170 (e.g., over the perimeter 173 of the opening 176 of the channel 175) and deposit in the channel 175. For example, in some embodiments, while collecting the material 184 from the channel 175 with the collecting-port 183 (See FIG. 13), at least a portion of the predetermined amount of liquid 180 and the added material 182 (including waste material 184) may remain within the region 142 of the cell culture chamber 103 based, at least in part, on the orientation of the vessel 100 and the presence of the flange 170 preventing at least the portion of the predetermined amount of liquid 180 and the added material 182 (including waste material 184) within the region 142 from flowing into the channel 175. Thus, in some embodiments, by moving the vessel 100 to cause at least a portion of the predetermined amount of liquid 180 and the added material 182 (including waste material 184) to flow from the region 142 over the flange 170 and deposit in the channel 175, removal of the waste material 184 can be controlled and, in some embodiments, increased relative to, for example, a method where the vessel 100 is not moved. In some embodiments, the angle of the axis 110 relative to the direction of gravity "g" defined by the second orientation of the vessel 100 (See FIG. 14) can be selected to, for example, cause at least a portion of the predetermined amount of liquid 180 and the added material 182 (including waste material 184) to flow from the region 142 over the flange 170 and deposit in the channel 175 without causing cells 150 being cultured in the plurality of microcavities 120 from dislodging, thereby improving the cell culturing process.

Accordingly, in some embodiments, moving the vessel 100 in accordance with embodiments of the disclosure to cause at least a portion of the predetermined amount of liquid 180 and the added material 182 (including waste material 184) to flow from the region 142 over the flange 170 and deposit in the channel 175 as well as collecting the material 184 from the channel 175 with the collecting-port 183 can provide removal of all or at least a greater quantity of waste material 184 from the cell culture chamber 103, as compared to other methods, including but not limited to methods where the vessel 100 is not moved (e.g., remains stationary). In some embodiments, the orientation of the axis 110 of the vessel 100 (e.g., relative to the direction of gravity "g") can remain unchanged during a duration of time while collecting the material 184 from the channel 175 with the collecting-port 183. Alternatively, in some embodiments, the orientation of the axis 110 of the vessel 100 (e.g., relative to the direction of gravity "g") can change one or more times during a duration of time while collecting the material 184 from the channel 175 with the collecting-port 183.

Figure 15:
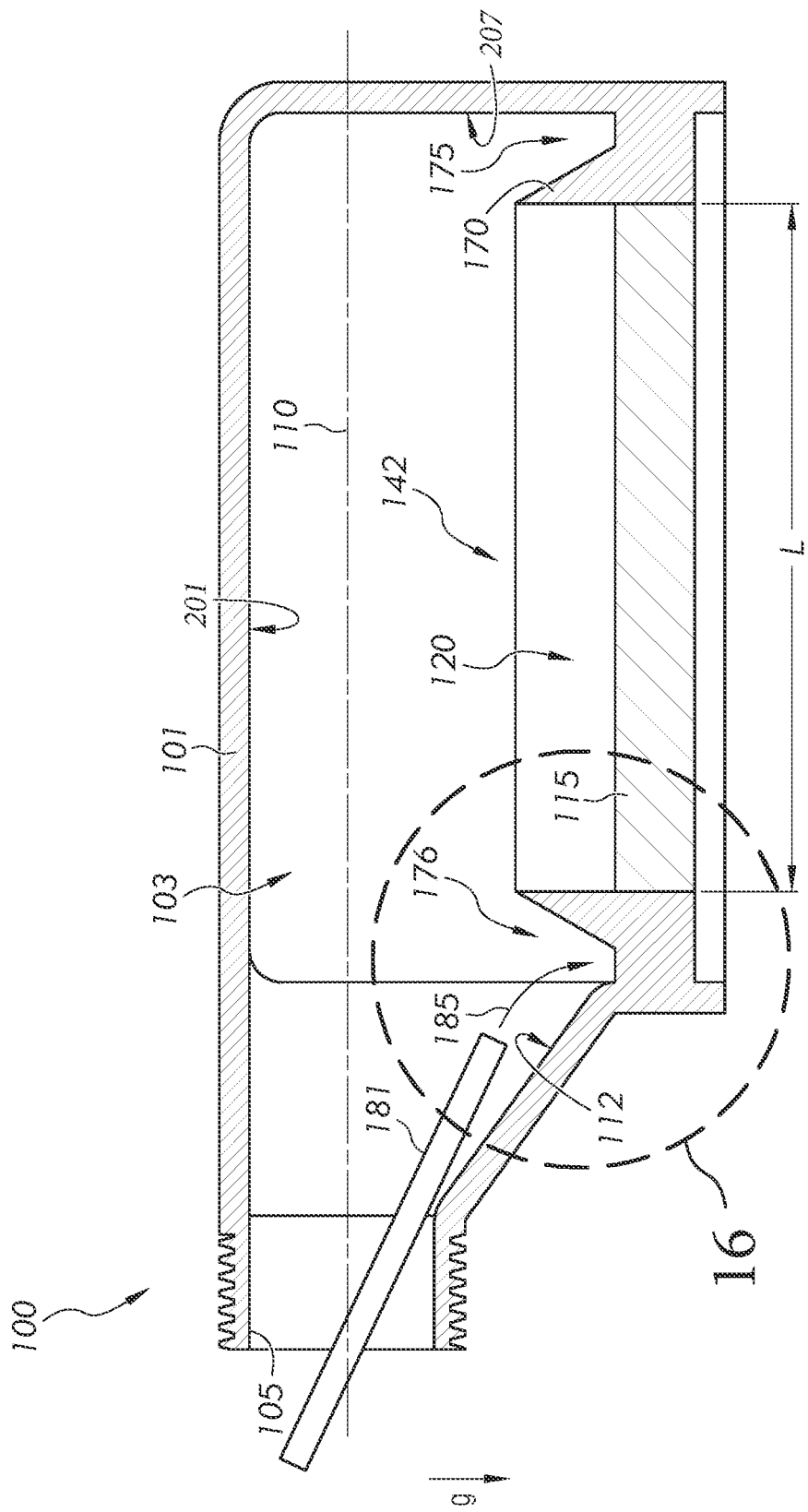
FIG. 15 shows an embodiment of the cell culture vessel of FIG. 4 including a method of adding material to the channel with a dispensing-port in accordance with embodiments of the disclosure.

Additionally, as shown in FIG. 15, in some embodiments, the method can include adding material (e.g., food, nutrients) into the cell culture chamber 103 by inserting the dispensing-port 181 into the aperture 105 and dispensing material 185 from the dispensing-port into the opening 176 of the channel 175 after removing material 184 (e.g., waste) from the cell culture chamber 103 (See FIG. 12-14). For example, FIG. 15 schematically shows waste material 184 removed from the cell culture chamber 103 after collecting the material 184 from the channel 175 with the collecting-port 183 (See FIG. 69) and after moving the vessel 100 to cause at least a portion of the predetermined amount of liquid 180 and the added material 182 (including waste material 184) to flow from the region 142 over the flange 170 and deposit in the channel 175 (See FIG. 14). In some embodiments, the added material 185 can, for example, replenish the cell culture environment with food and nutrients which the cells 150 have consumed and/or depleted. Thus, in some embodiments, the material 182 and material 185 can include a same or similar composition or different compositions depending on, for example, the type of cell culturing being performed in the vessel 100. Moreover, in some embodiments, the methods of adding material 182 (e.g., food, nutrients) (See FIG. 11 and FIG. 12), removing material 184 (e.g., waste) (See FIGS. 12-14), and adding more material 185 (e.g., food, nutrients) (See FIG. 15) can be performed selectively one time or multiple times, while culturing cells 150, as the spheroids 150a, 150b, 150c continually (e.g., repeatedly) consume media (e.g., food, nutrients) and/or produce metabolite (e.g., waste) as a byproduct during the cell culturing process.

Figure 16:
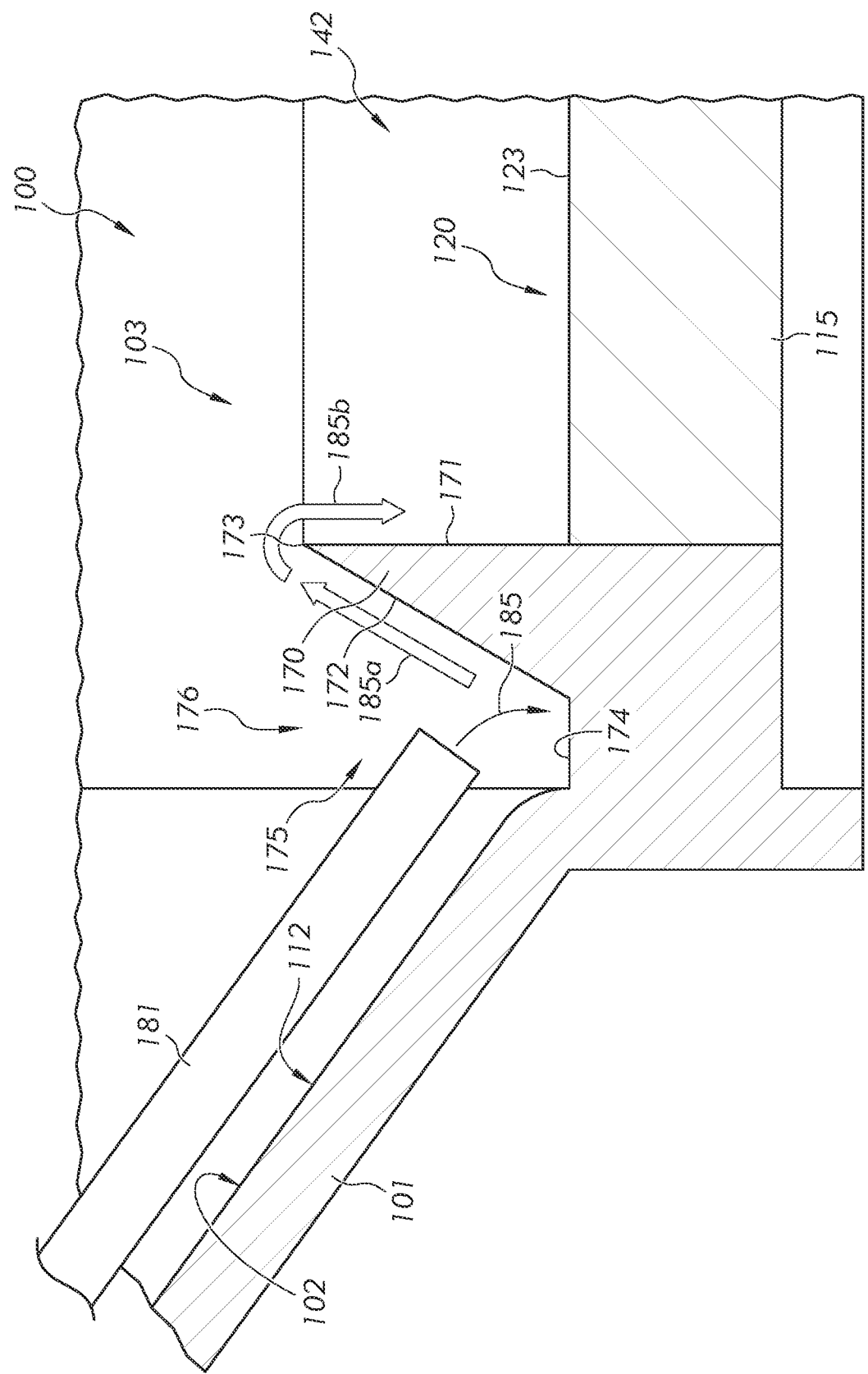
FIG. 16 illustrates an enlarged schematic representation of an embodiment of a portion of the cell culture vessel taken at view 16 of FIG. 15 including the flange, the channel, and the method of adding material to the channel with a dispensing-port in accordance with embodiments of the disclosure.

In some embodiments, one or more features of the flange 170 and the channel 175 can provide advantages when adding and removing media (See FIG. 11-15) to avoid displacing the spheroids 150a, 150b, 150c from the microcavities 120a, 120b, 120c and promote desired cell culturing of the spheroids 150a, 150b, 150c (see FIGS. 7 and 8). For example, FIG. 16 illustrates an enlarged schematic representation of a portion of the cell culture vessel 100 taken at view 16 of FIG. 15 including the method of adding material 185 (e.g., food, nutrients) into the cell culture chamber 103 by inserting the dispensing-port 181 into the aperture 105 and dispensing material 185 from the dispensing-port 181 into the opening 176 of the channel 175. Similarly, FIG. 73 illustrates an enlarged schematic representation of a portion of the cell culture vessel 100 taken at view 73 of FIG. 68 including the method of removing material 184 (e.g., waste) from the cell culture chamber 103 by inserting the collecting-port 183 into the aperture 105 and collecting material 184 from the channel 175 with the collecting-port 183.

As shown in FIG. 16, in some embodiments, the method of adding material 185 (e.g., food, nutrients) into the cell culture chamber 103 by inserting the dispensing-port 181 into the aperture 105 and dispensing material 185 from the dispensing-port into the opening 176 of the channel 175 can include obstructing the flow of material 185 along a first flow path 185a, 185b. For example, in some embodiments, the obstructing the flow along the first flow path 185a, 185b can include diverting the flow along the first flow path 185a, 185b with the flange 170. In some embodiments, the diverting the flow along the first flow path 185a, 185b with the flange 170 can include, for example, filling the channel 175 with the material 185 along first flow path 185a, and then flowing the material 185 along first flow path 185b from the channel 175 into the region 142 of the cell culture chamber 103. For example, in some embodiments, the material 185 can be dispensed from the dispensing-port 181 into the opening 176 of the channel 175 to gradually fill the channel 175 with the material 185 along first flow path 185a from the base 174 of the channel 175 to the perimeter 173 of the opening 176 of the channel 175 along the outer face 172 of the channel 175. Additionally, in some embodiments, once the channel 175 is filled with material 185, the material 185 can then flow over the perimeter 173 of the opening 176 of the channel 175 into the region 142 of the cell culture chamber 103 along first flow path 185b.

Accordingly, in some embodiments, at least a portion of the region 142 (defined based at least in part by the inner face 171 of the flange 170 and the portion 123 of the substrate 115) as well as at least a portion of the cell culture chamber 103 can gradually fill with the material 185 while the material 185 is dispensed from the dispensing-port 181 into the opening 176 of the channel 175. Although described with respect to adding material 185 to the cell culture chamber 103, it is to be understood, unless otherwise noted, that at least a portion of the region 142 (defined based at least in part by the inner face 171 of the flange 170 and the portion 123 of the substrate 115) as well as at least a portion of the cell culture chamber 103 can gradually fill with the material 182 while the material 182 is dispensed from the dispensing-port 181 into the opening 176 of the channel 175, as shown in FIG. 11.

Figure 17:
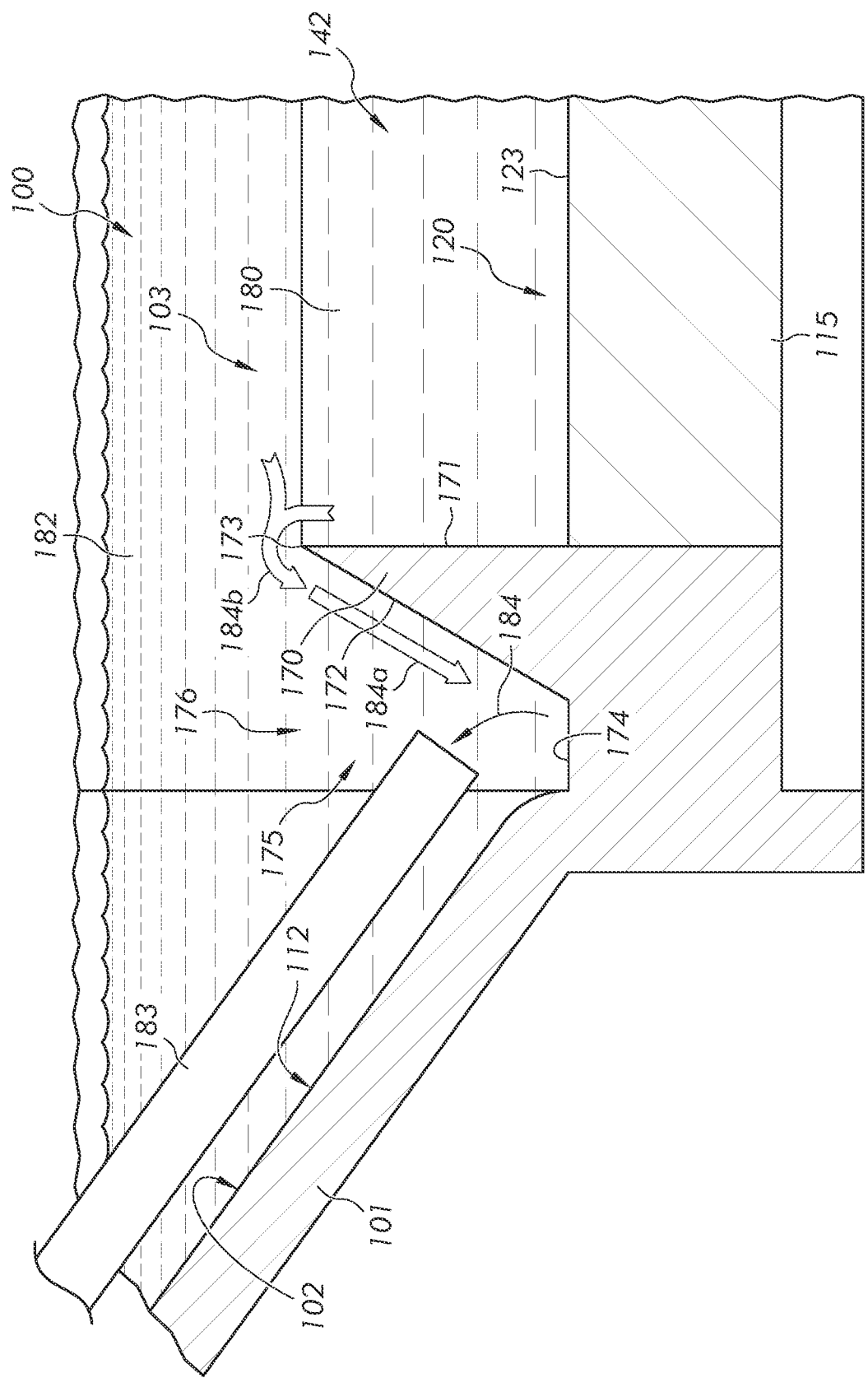
FIG. 17 illustrates an enlarged schematic representation of an embodiment of a portion of the cell culture vessel taken at view 16 of FIG. 15 including the flange, the channel, and the method of removing material from the channel with a collecting-port in accordance with embodiments of the disclosure.

Likewise, as shown in FIG. 17 in some embodiments, the method of removing material (e.g., waste) from the cell culture chamber 103 by inserting the collecting-port 183 into the aperture 105 and collecting material 184 from the channel 175 with the collecting-port 183 can include obstructing the flow of material 184 along a second flow path 184a, 184b. For example, in some embodiments, the obstructing the flow along the second flow path 184a, 184b can include diverting the flow along the second flow path 184a, 184b with the flange 170. In some embodiments, the diverting the flow along the second flow path 184a, 184b with the flange 170 can include, for example, removing the material 184 from the channel 175 along second flow path 184a, while flowing the material 184 along second flow path 184b. In some embodiments, second flow path 184b can extend from the region 142 of the cell culture chamber 103 into the channel 175. In addition or alternatively, based at least in part on, for example, a volume of material 180, 182, 184 contained within the cell culture chamber 103, in some embodiments, second flow path 184b can extend from the cell culture chamber 103 (e.g., outside the region 142) into the channel 175.

Accordingly, in some embodiments, the material 184 can be collected from the channel 175 with the collecting-port 183 to gradually remove the material 184 from the channel 175 along the second flow path 184a, 184b. Additionally, in some embodiments, for example, after moving the vessel 100 to cause at least a portion of the predetermined amount of liquid 180 and the added material 182 (including waste material 184) to flow from the region 142 over the flange 170 and deposit in the channel 175 (See FIG. 14), the material 184 can be collected from the channel 175 with the collecting-port 183 to gradually remove the material 184 from the channel 175 along the second flow path 184a, 184b. For example, material 184 can be gradually removed from the channel 175 along second flow path 184a from the perimeter 173 of the opening 176 of the channel 175 along the outer face 172 of the channel 175 to the base 174 of the channel 175. Accordingly, in some embodiments, the material 184 can be gradually removed from at least a portion of the cell culture chamber 103 as well as from at least a portion of the region 142 (defined based at least in part by the inner face 171 of the flange 170 and the portion 123 of the substrate 115) while the material 184 is collected with the collecting-port 183 from the channel 175.

In some embodiments, while culturing cells 150 in at least one microcavity 120a, 120b, 120c of the plurality of microcavities 120, obstructing the flow of material 185 along the first flow path 185a, 185b with the flange 170 and obstructing the flow of material 184 along the second flow path 184a, 184b with the flange 170 can respectively add and remove material from the cell culture chamber 103 of the vessel 100 without, for example, interfering with the culturing of the cells 150. For example, as shown in FIG. 72, in some embodiments, the dispensing-port 181 can add material 185 to the cell culture chamber 103 by flowing (e.g., dispensing, blowing, aspirating) the material 185 from the dispensing-port 181 into the channel 175 with a velocity along the first flow path 185a, 185b, thereby creating a positive pressure force in and around the channel 175. Likewise, as shown in FIG. 73, in some embodiments, the collecting-port 183 can remove material 184 from the cell culture chamber 103 by flowing (e.g., collecting, sucking) the material from the channel 175 into the collecting-port 183 with a velocity along the second flow path 184a, 184b, thereby creating a negative pressure force in and around the channel 175. Accordingly, in some embodiments, the flange 170 can slow a velocity of the material 185, 184 respectively flowing along the first flow path 185a, 185b and the second flow path 184a, 184b, thereby respectively decreasing the positive pressure force and the negative pressure force in and around channel 175.

For example, in some embodiments, the method of adding material (e.g., food, nutrients) into the cell culture chamber 103 by inserting the dispensing-port 181 into the aperture 105 and dispensing material 185 from the dispensing-port into the opening 176 of the channel 175 (See FIG. 16) can provide a slow, continuous, and controlled (e.g., non-turbulent) flow of material 185 into the cell culture chamber 103 as compared to, for example, a method or cell culture vessel not including one or more features of the flange 170 and the channel 175. Likewise, in some embodiments, the method of removing material (e.g., waste) from the cell culture chamber 103 by inserting the collecting-port 183 into the aperture 105 and collecting material 184 from the channel 175 (See FIG. 17) can provide a slow, continuous, and controlled (e.g., non-turbulent) flow of material 184 out of the cell culture chamber 103 as compared to, for example, a method or cell culture vessel not including one or more features of the flange 170 and the channel 175. By reducing a velocity of the material 185, 184 respectively flowing along the first flow path 185a, 185b and the second flow path 184a, 184b, in some embodiments, the flange 170 and the channel 175 can, therefore, prevent cells 150 being cultured in at least one microcavity 120a, 120b, 120c of the plurality of microcavities 115 from dislodging. For example, in some embodiments, if flow of material dislodges one or more cells 150, one or more microcavities 120a, 120b, 120c can include more than one spheroid or no spheroids. Accordingly, in some embodiments, by providing a slow, continuous, and controlled (e.g., non-turbulent) flow of material, based at least in part on one or more features of the flange 170 and the channel 175, in accordance with methods and embodiments of the disclosure, the likelihood of dislodging cells 150 being cultured in the vessel 100 can be reduced and better quality cell cultures and more accurate scientific results relating to the cell cultures can be obtained.

Example 1: Cell Growth

HCT116, a colon cancer cell line, was grown to ~80% confluency in a flask in complete McCoy's 5a media (10% fetal bovine serum with 10 units/mL of penicillin/10 µg/mL streptomycin) and trypsinized to detach the cells from the surface. The cells were then counted and resuspended in complete McCoy's media at a final concentration of cells at 1000 cells per microcavity (for T-75 microcavity flask add 15 mL of cells at final concentration of ~6.5×10^5 cells/mL). Allow microcavity flask to sit at room temperature to allow for the cells to settle into the surface of the microcavity flask. After room temperature incubation, place flask in to 37° C. incubator with 5% CO2 and 95% relative humidity for the duration of the experiment. Spheroid formation occurs within the first 24 hours.

Control Flask: HTC116 cells were seeded into a T75 flask that was prepared by cutting away the bottom surface of the flask and affixing material having an array of microcarriers to the bottom of the flask. Because the flask was cut away, a "lip" of material remained around the inner periphery of the bottom surface of the flask. This flat surface, around the periphery of the array of microcavities, was present during culture in the control vessel.

Experimental Flask: HTC116 cells were also seeded into a T75 flask having the flange and channel structure illustrated in FIGS. 4 and 5, for example.

After media with suspended cells were added to the inner area, flask was allowed to stay in static conditions for 15 min at room temperature to allow cells to settle into microwells. This 15 min incubation step is used in cell culture biology labs to ensure uniform cell seeding and to minimize edge effects upon subsequent placement of the vessels into incubator chamber. After cells settled into the microcavities, an additional amount of cell culture media was then added to the flask. In the control flask, media was added with a pipette to the mid-center of the bottom surface of the flask. In the experimental flask, media was added as shown, for example, in FIG. 16. The flask was then placed into cell culture incubator and cultured for 14 days. During this culture period total of 7 media exchanges, with 90% media exchange efficiency, were performed.

Figure 18B:
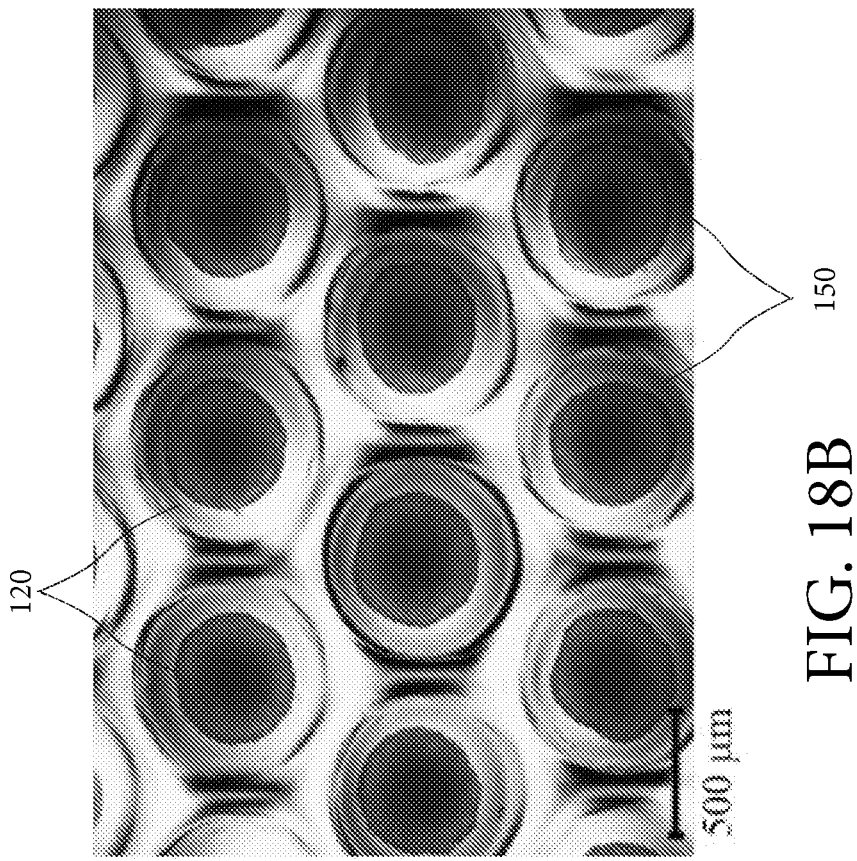
FIG. 18B is a photographs of spheroids growing in a flask with the flange and channel structures, according to an embodiments.
Figure 18A:
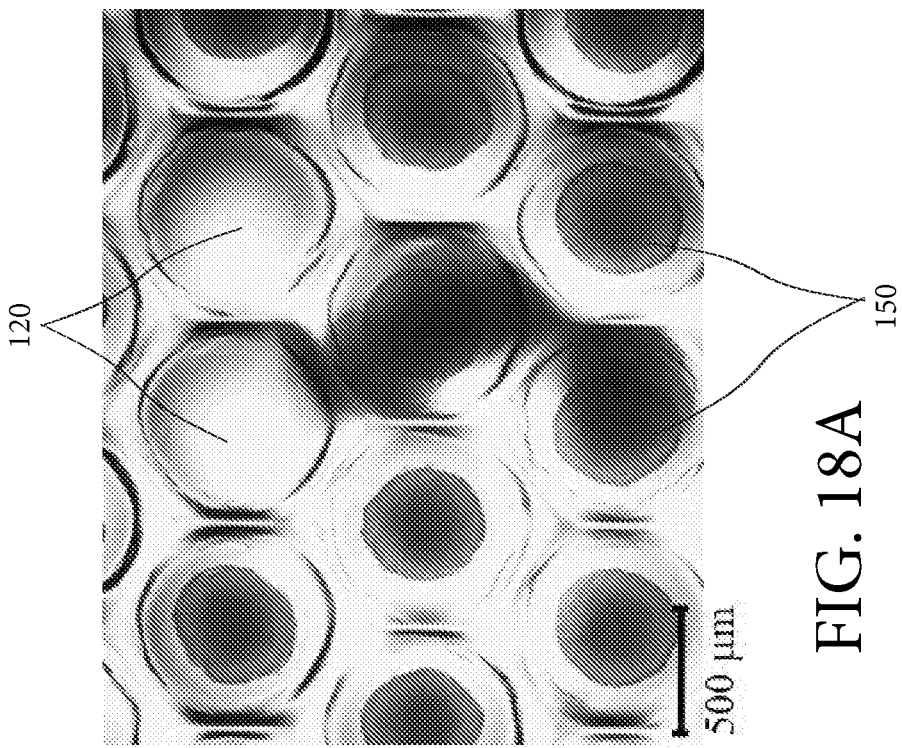
FIG. 18A is a photograph of spheroids growing in a T175 flask without the flange and channel structures.

FIG. 18A is a photograph of spheroids growing in the control T75 flask. Spheroids are irregular and missing from some microcavities (having possibly been dislodged during media changes). In addition, irregular cellular conglomerates were seen in the control flask, such as those shown in FIGS. 3A and 3B. FIG. 18B is a photograph showing spheroids in the experimental flask after 14 days of culture. Spheroids appear to be similar in size and all wells are filled with spheroids. FIG. 18B demonstrates 100% spheroid retention in the flask assembled according to the experimental design with media changes.

Figure 19C:
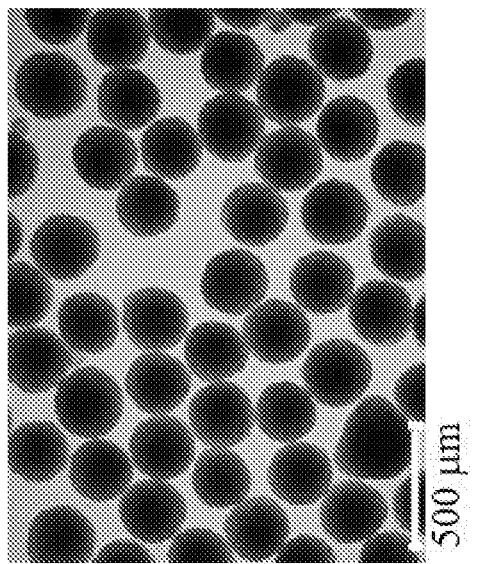
FIGS. 19A, 19B, 19C and 19D are photographs of cells harvested following 14 days of culture from the control flask (FIGS. 19A and 19B) and from the experimental flask of, for example, FIG. 4 (FIG. 19C and FIG. 19D).
Figure 19D:
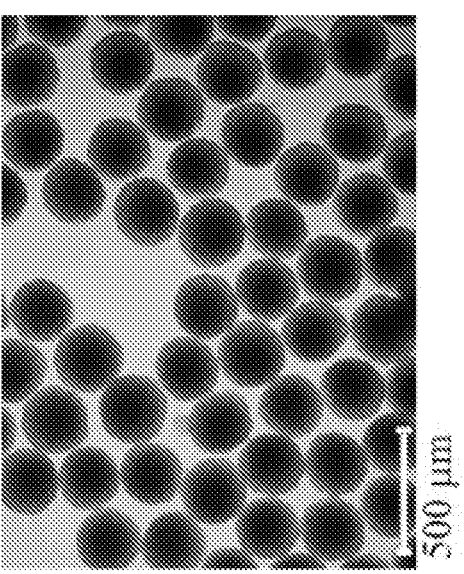
Figure 19A:
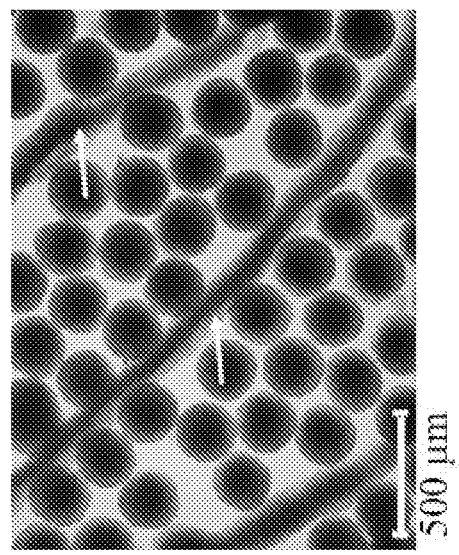
Figure 19B:
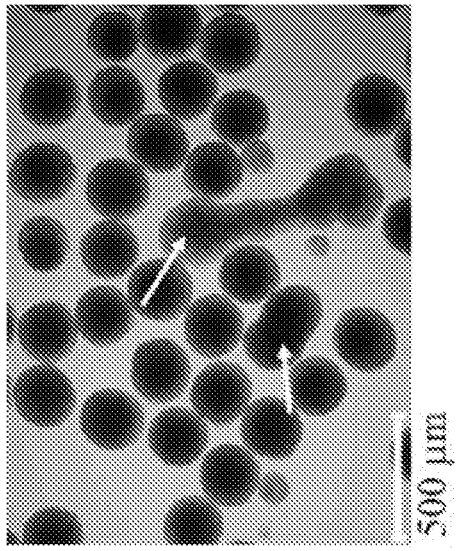

Following 14 days of culture, spheroids were harvested from the control flask (FIGS. 19A and 19B) and from the experimental flask of, for example, FIG. 4 (FIG. 19C and FIG. 19D). FIGS. 19A, 19B, 19C and 19D are photographs of the harvested cells. As is seen in FIG. 19A, cells formed "ropes" of cells in vessels that had flat surfaces in the cell culture area (see white arrows). Other irregular cellular conglomerates can be seen in FIG. 19B. In contrast, spheroids grown in the experimental flask according to FIG. 4 were regular and homogeneous, as shown in FIG. 19C and FIG. 19D.

In embodiments, the disclosure provides, in a first aspect, a cell culture vessel having a top, a bottom, sidewalls and a necked opening; a substrate on the bottom of the vessel comprising a plurality of microcavities, each microcavity of the plurality of microcavities comprising a well opening and a concave well bottom; an angled flange surrounding the outer perimeter of the substrate, wherein the flange has an inner face adjacent to the substrate and an outer face opposite the substrate.

A number of aspects of cell culture vessels and methods of culturing cells have been disclosed herein. A summary of some selected aspects is presented below.

In a second aspect, the disclosure proved the cell culture vessel of aspect 1, wherein the substrate is affixed to the bottom of the vessel.

In a third aspect, the disclosure provides the cell culture vessel of aspect 1 wherein the substrate is integral to a bottom surface of the vessel.

In a fourth aspect, the disclosure provides the cell culture vessel of aspect 1 wherein the substrate is integral to a bottom surface of the vessel.

In a fourth aspect, the disclosure provides the cell culture vessel of aspect 1 wherein the outer face of the flange is angled.

In a fifth aspect, the disclosure provides the cell culture vessel of aspect 2 wherein outer face of the flange is angled.

In a sixth aspect, the disclosure provides the cell culture vessel of aspect 3 wherein the outer face of the flange is angled.

In a seventh aspect, the disclosure provides the cell culture vessel of aspect 1, further comprising a channel surrounding the outer perimeter of the angled flange, forming a moat around the substrate on the outer side of the flange.

In an eighth aspect, the disclosure provides the cell culture vessel of aspect 2 further comprising a channel surrounding the outer perimeter of the angled flange, forming a moat around the substrate on the outer side of the flange.

In a ninth aspect, the disclosure provides the cell culture vessel of aspect 3 further comprising a channel surrounding the outer perimeter of the angled flange, forming a moat around the substrate on the outer side of the flange.

In a tenth aspect, the disclosure provides the cell culture vessel of aspect 4 further comprising a channel surrounding the outer perimeter of the angled flange, forming a moat around the substrate on the outer side of the flange.

In an eleventh aspect, the disclosure provides the cell culture vessel of aspect 5 further comprising a channel surrounding the outer perimeter of the angled flange, forming a moat around the substrate on the outer side of the flange.

In a twelfth aspect, the disclosure provides the cell culture vessel of aspect 6 further comprising a channel surrounding the outer perimeter of the angled flange, forming a moat around the substrate on the outer side of the flange.

In a thirteenth aspect, the disclosure provides a method of culturing cells in the cell culture vessel of aspect 1, comprising: depositing liquid into the cell culture vessel on the neck-side of the flange; filling the vessel with liquid until the liquid spills over the flange onto the substrate comprising a plurality of microcavities; culturing cells in the plurality of microcavities.

In a fourteenth aspect, the disclosure provides the method of aspect 13 further comprising after culturing, tilting the cell culture vessel to accumulate cell liquid in the channel; inserting a collecting port into the aperture of the vessel and using the collecting port to remove liquid from the channel.

Throughout the disclosure, the terms "material", "liquid", and "gas" can be used to describe properties of a material employed when, for example, culturing cells in the cell culture vessel. Unless otherwise noted, for purposes of the disclosure, "material" can include fluid material (e.g., liquid or gas). Additionally, material can include a culture solution or media including a liquid including solid particles (e.g., cells) suspended in the liquid. Unless otherwise noted, for purposes of the disclosure, "liquid" can include cleaning or rinsing solutions, aqueous solutions, or other liquid that can be added to or removed from the vessel to, for example, clean the cell culture chamber, sterilize one or more features of the substrate and the vessel, prepare the substrate for cellular growth and other uses of liquid. Additionally, liquid can include a culture solution or media including a liquid including solid particles (e.g., cells) suspended in the liquid. Unless otherwise noted, for purposes of the disclosure, "gas" can include air, filtered or treated air, or other gases.

Throughout the disclosure, the terms "non-permeable", "gas-permeable", and "porous" can be used to describe properties (e.g., material properties, characteristics, parameters) of one or more features of a substrate.

Unless otherwise noted, for purposes of the disclosure, a "non-permeable" substrate (e.g., material of a non-permeable substrate) is considered to be impermeable to solid, liquid, and gas under normal conditions (e.g., no external influence including but not limited to pressure and force) and, therefore, does not permit the transfer of solid, liquid, or gas in to, through, or out of, the non-permeable substrate under normal conditions. In some embodiments, a non-permeable substrate can form a portion of the wall of the vessel. Additionally, the cell culture chamber of the vessel is considered to be sterile when a non-permeable substrate forms a portion of the wall of the vessel because bacteria, for example, cannot pass through the non-permeable substrate. However, when filling the plurality of microcavities of the substrate with material, gas can become trapped within the microcavity of a non-permeable substrate based on surface tension of the liquid, thereby, in some embodiments, preventing material from filling the microcavities and preventing growth of a spheroid.

Unless otherwise noted, for purposes of the disclosure, a "gas-permeable" substrate (e.g., material of a gas-permeable substrate) is considered to be impermeable to solid and liquid, and permeable to gas under normal conditions. Therefore, a gas-permeable substrate does not permit the transfer of solid and liquid in to, through, or out of, the gas-permeable substrate and does permit the transfer of gas in to, through, or out of, the gas-permeable substrate. In some embodiments, a gas-permeable substrate can form a portion of the wall of the vessel. Additionally, the cell culture chamber of the vessel is considered to be sterile when a gas-permeable substrate forms a portion of the wall of the vessel because bacteria, for example, cannot reasonably pass through the gas-permeable substrate. However, although the substrate is gas-permeable, gas can still become trapped in the microcavity during filling with material because gas-permeation rates through the gas-permeable substrate can be slower than the rate required to displace gas from the cavity under ordinary operating conditions and can therefore take an unacceptably long amount of time to permeate through the substrate. Thus, in some embodiments, slowly filling the microcavities allows the liquid front to enter each microcavity at an angle, thereby displacing gas as the liquid fills the microcavity. In some embodiments, after filling the cavity with liquid, gas can permeate (slowly) through the gas-permeable substrate.

Unless otherwise noted, for purposes of the disclosure, a "porous" substrate (e.g., material of a porous substrate) is considered to be impermeable to solid and permeable to liquid and gas under normal conditions. Therefore, a porous substrate does not permit the transfer of solid in to, through, or out of, the porous substrate and does permit the transfer of liquid and gas in to, through, or out of, the porous substrate. A porous substrate cannot form a portion of the vessel because bacteria can pass through a porous substrate, thus causing sterility issues in the cell culture chamber. Thus, when using a porous substrate, the substrate must be enclosed (entirely enclosed) in the sterile cell culture chamber of the vessel. During filling of the microcavities with material, however, gas can escape (e.g., pass) through the porous substrate. Thus, filling of the microcavities can be performed rapidly without concern for entrapping gas in the microcavities. In some embodiments, liquid can only pass through the porous substrate with added pressure or physical contact and disturbance of the substrate. Thus, in some embodiments, material including liquid can be contained in the microcavities of the substrate so long as the substrate is not exposed to added pressure or physical contact and disturbance. For example, in some embodiments, the porous substrate can be supported in the cell culture chamber to allow gas to pass through the substrate during filling as well as during culturing and to isolated the substrate from added pressure or physical contact and disturbance from external forces (e.g., outside the cell culture chamber).

It will be appreciated that the various disclosed embodiments can involve particular features, elements or steps that are described in connection with that particular embodiment. It will also be appreciated that a particular feature, element or step, although described in relation to one particular embodiment, can be interchanged or combined with alternate embodiments in various non-illustrated combinations or permutations.

It is to be understood that, as used herein the terms "the," "a," or "an," mean "at least one," and should not be limited to "only one" unless explicitly indicated to the contrary. Thus, for example, reference to "a component" includes embodiments having two or more such components unless the context clearly indicates otherwise.

Ranges can be expressed herein as from "about" one particular value, and/or to "about" another particular value. When such a range is expressed, embodiments include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments can be disclosed using the transitional phrase "comprising," it is to be understood that alternative embodiments, including those that can be described using the transitional phrases "consisting" or "consisting essentially of," are implied. Thus, for example, implied alternative embodiments to an apparatus that comprises A+B+C include embodiments where an apparatus consists of A+B+C and embodiments where an apparatus consists essentially of A+B+C.

It will be apparent to those skilled in the art that various modifications and variations can be made to the present disclosure without departing from the spirit and scope of the disclosure. Thus, it is intended that the present disclosure cover the modifications and variations of this disclosure provided they come within the scope of the appended claims and their equivalents.

What is claimed is:

1. A cell culture vessel comprising:
a top, a bottom, sidewalls and a necked opening;
a substrate on the bottom of the vessel comprising a plurality of microcavities, each microcavity of the plurality of microcavities comprising a well opening and a concave well bottom; and
an angled flange surrounding a portion of the substrate and extending in a direction away from the substrate to define a perimeter at a top of the flange,
wherein the flange has an inner face adjacent to the portion of the substrate and an outer face opposite the portion of the substrate the inner face extending in a vertical direction from the substrate to the perimeter, and the outer face extends at an angle from the perimeter to the substrate.

2. The cell culture vessel of claim 1, wherein the substrate is affixed to the bottom of the vessel.

3. The cell culture vessel of claim 1, wherein the substrate is integral to a bottom surface of the vessel.

4. The cell culture vessel of claim 1, wherein the outer face of the flange is angled from the perimeter to a base of a channel.

5. The cell culture vessel of claim 1 further comprising a channel surrounding the outer perimeter of the angled flange, forming a moat around the substrate on the outer side of the flange.

6. The cell culture vessel of claim 2, further comprising a channel surrounding the outer perimeter of the angled flange, forming a moat around the substrate on the outer side of the flange.

7. The cell culture vessel of claim 3, further comprising a channel surrounding the outer perimeter of the angled flange, forming a moat around the substrate on the outer side of the flange.

8. A method of culturing cells in the cell culture vessel of claim 1, comprising:
depositing liquid into the cell culture vessel on the neck-side of the flange;
filling the vessel with liquid until the liquid spills over the flange onto the substrate comprising a plurality of microcavities; and
culturing cells in the plurality of microcavities.

9. The method of claim 8, further comprising:
after culturing, tilting the cell culture vessel to accumulate cell liquid in the channel;
inserting a collecting port into the aperture of the vessel and using the collecting port to remove liquid from the channel.

* * * * *